United States Patent
Davis et al.

(10) Patent No.: US 11,413,220 B2
(45) Date of Patent: Aug. 16, 2022

(54) VENTED AIR RELEASE COUPLING AND METHOD OF USING THE SAME

(71) Applicant: Avent, Inc., Alpharetta, GA (US)

(72) Inventors: Benjamin M. Davis, Woodstock, GA (US); David A. Doornbos, Woodstock, GA (US)

(73) Assignee: Avent, Inc., Alpharetta, GA (US)

( * ) Notice: Subject to any disclaimer, the term of this patent is extended or adjusted under 35 U.S.C. 154(b) by 321 days.

(21) Appl. No.: 16/255,196

(22) Filed: Jan. 23, 2019

(65) Prior Publication Data
US 2019/0224079 A1   Jul. 25, 2019

Related U.S. Application Data

(60) Provisional application No. 62/620,576, filed on Jan. 23, 2018.

(51) Int. Cl.
| | | |
|---|---|---|
| *A61J 15/00* | (2006.01) | |
| *A61J 7/00* | (2006.01) | |
| *A61M 39/10* | (2006.01) | |
| *A61M 39/20* | (2006.01) | |

(52) U.S. Cl.
CPC ......... *A61J 15/0096* (2013.01); *A61J 7/0053* (2013.01); *A61J 15/0076* (2015.05); *A61M 39/10* (2013.01); *A61M 39/20* (2013.01); *A61M 2039/205* (2013.01)

(58) Field of Classification Search
CPC .............. A61J 15/0092; A61J 15/0096; A61M 2039/205; A61M 39/10; A61M 39/20
See application file for complete search history.

(56) References Cited

U.S. PATENT DOCUMENTS

| | | | | |
|---|---|---|---|---|
| 4,043,334 | A | * | 8/1977 | Brown ................ A61M 5/3134 |
| | | | | 604/199 |
| 4,202,334 | A | | 5/1980 | Elson |
| 4,576,595 | A | * | 3/1986 | Aas ..................... B01L 3/50825 |
| | | | | 604/256 |
| 5,377,854 | A | * | 1/1995 | Cusack ................ B65D 51/241 |
| | | | | 215/307 |
| 6,027,482 | A | * | 2/2000 | Imbert ................ A61M 5/3134 |
| | | | | 604/240 |
| 6,491,667 | B1 | | 12/2002 | Keane et al. |
| RE40,428 | E | | 7/2008 | Keane et al. |
| 8,298,196 | B1 | | 10/2012 | Mansour |
| 8,506,549 | B2 | | 8/2013 | Breuer-Thal et al. |

(Continued)

FOREIGN PATENT DOCUMENTS

KR          485261 Y1 * 12/2017

OTHER PUBLICATIONS

International Application No. PCT/US2019/014728, International Search Report and Written Opinion dated Mar. 21, 2019, 13 pages.

*Primary Examiner* — William R Carpenter
(74) *Attorney, Agent, or Firm* — Dority & Manning, P.A.

(57) ABSTRACT

An ISO 80369-3 compatible coupling having at least one vent, recessed groove, non-cylindrical geometry and/or textured surface formed therewith. According to one example embodiment, a vent can be formed on a male coupling and/or a female coupling. The vent can be in the form of recessed channel. According to one example embodiment, the coupling comprises non-cylindrical geometry such that at least one vent is provided.

28 Claims, 24 Drawing Sheets

(56) References Cited

U.S. PATENT DOCUMENTS

| | | | |
|---|---|---|---|
| 8,992,488 | B2 | 3/2015 | Ingram et al. |
| 9,028,438 | B2 | 5/2015 | Ingram et al. |
| 9,308,362 | B2 | 4/2016 | Mansour et al. |
| 9,757,522 | B2 | 9/2017 | Ingram et al. |
| 10,589,080 | B2 * | 3/2020 | Hitchcock ............... B65D 41/02 |
| 2011/0240162 | A1 * | 10/2011 | Zeyfang ................ A61M 39/20 138/89.2 |
| 2014/0039462 | A1 | 2/2014 | Ingram et al. |
| 2014/0188089 | A1 * | 7/2014 | Midgette ............... A61L 31/048 604/539 |
| 2016/0030293 | A1 | 2/2016 | Dorsey et al. |
| 2016/0067422 | A1 * | 3/2016 | Davis .................. A61M 5/3202 604/192 |
| 2016/0067471 | A1 | 3/2016 | Ingram et al. |
| 2016/0121054 | A1 | 5/2016 | Truitt et al. |
| 2016/0367439 | A1 | 12/2016 | Davis et al. |
| 2017/0189618 | A1 * | 7/2017 | Ward ................... B65G 11/023 |
| 2017/0312181 | A1 | 11/2017 | Davis et al. |
| 2017/0319438 | A1 * | 11/2017 | Davis ................. A61M 39/1011 |
| 2018/0256881 | A1 | 9/2018 | Hitchcock et al. |
| 2018/0280681 | A1 | 10/2018 | Ingram et al. |

\* cited by examiner

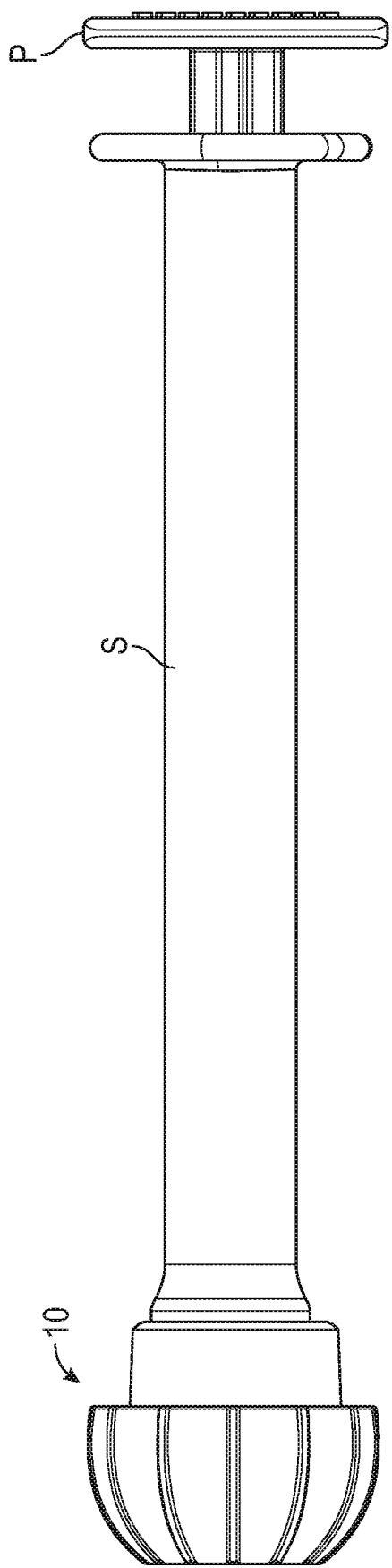

VENTED AIR RELEASE COUPLING AND METHOD OF USING THE SAME

CORRESPONDING APPLICATIONS

This application claims priority to U.S. Patent Application No. 62/620,576 filed on Jan. 23, 2018, which is hereby incorporated by reference.

TECHNICAL FIELD

The present invention relates generally to the field of enteral feeding and fluid transfer devices, and more particularly to vented couplings and connectors.

SUMMARY

In example embodiments, the present invention provides an enteral connector including a coupling having one or more vent features for allowing venting of a pocket, cavity or reservoir that is defined by the coupling during engagement with a complementary coupling.

In one aspect, the present invention relates to a tip cap comprising an ENFit compatible male coupling comprising at least one recessed channel extending along an outer periphery thereof, from a tip end and extending a distance therefrom. In some example embodiments, one or more recessed channels, vents, textured surfaces, noncylindrical geometries and/or a combination thereof can be provided for the purposes of facilitating venting.

In another aspect, the invention relates to an ISO 80369-3 compatible coupling (commonly referred to as ENFit) having a male coupler. The male coupler includes an outer surface. The outer surface includes one or more recessed grooves or vents formed therein. Optionally, the male coupler can comprise a texturized surface formed thereon, or for example, can comprise a non-circular geometry, or a combination thereof.

In other aspects, the present disclosure relates generally to an ISO 80369-3 formatted coupling comprising a male coupler, the male coupler comprising an outer surface, the outer surface comprising one or more vents formed therein. The male coupler can be formed with a tip cap. The tip cap further comprises an outer collar surrounding the male coupler. The outer collar comprises a substantially smooth interior surface without any threads provided thereon. The male coupler of the tip cap can be configured for frictional engagement with an ISO 80369-3 compatible female coupling. The tip cap further comprises an outer collar that comprises a fully-threaded interior for compatible engagement with one or more lugs or threads of an ISO 80369-3 compatible coupling. The tip cap comprises an outer collar that is at least partially threaded for compatible engagement with one or more lugs or threads of an ISO 80369-3 compatible coupling. The tip cap comprises one or more clips for releasable engagement with a female coupler. The one or more clips comprise a threaded portion formed on an inner surface for complementary engagement with one or more threads or lugs of the female coupling FC. The male coupler of the tip cap is configured for a sealed interference fit with a female coupler. The male coupler is formed with a syringe-to syringe coupler. The male coupler can be formed with a fluid transfer connector. The male coupler can be formed with a syringe. The male coupler is formed with an oral administration coupler. The male coupler can be formed with a press-in bottle adaptor. The male coupler is formed with a vented connector. The male coupler can be formed with a fluid transfer lid.

According to another aspect, the present disclosure relates to an ISO 80369-3 compatible coupling configured for removable sealing engagement with an enteral syringe comprising a female coupling, an internal chamber and a plunger translating therein, the enteral syringe female coupling comprising a reservoir defined by an open distal end and a tapering inner surface, the ISO 80369-3 compatible coupling comprising: a male coupler comprising a tapering outer surface and a reservoir defined by an open distal end and an inner surface, the male coupler oriented along a connection axis, the male coupler tapering outer surface configured for removable sealing engagement with an enteral syringe female coupling tapering inner surface along a connection axis, the male coupler reservoir is configured to receive a volume of air; wherein, the male coupler tapering outer surface comprises at least one vent configured to release an amount of the volume of air present in the male coupling reservoir during engagement between the ISO 80369-3 compatible coupling and the enteral syringe.

Optionally, the male coupler tapering outer surface extends between a base end and a free end, wherein the at least one vent extends along the male coupler tapering outer surface from the free end toward the base end. Optionally, the male coupler tapering outer surface defines a range of diameters between a maximum diameter at a base end and a minimum diameter at a free end, the at least one vent being recessed from the range of diameters of the male coupler tapering outer surface. Optionally, the male coupler tapering outer surface range of diameters corresponds opposingly with the enteral syringe female coupling tapering inner surface, the at least one vent configured to be removed from sealing engagement with the enteral syringe female coupling tapering inner surface. Optionally, the male coupler inner surface comprises tapering section extending between an open section proximal to the open distal end and an opposite closed section, the at least one vent extending a distance along the tapering outer surface from a position relative to the connection axis in alignment with the open distal tip to a position relative to the connection axis in alignment with the inner surface tapering section. Optionally, the male coupler tapering outer surface comprises a plurality of the vents. Optionally, the at least one vent comprises a surface configured to be removed from engagement with the enteral syringe female coupling tapering inner surface during engagement between the ISO 80369-3 compatible coupling and the enteral syringe. Optionally, the at least one vent comprises a groove recessed from the male coupler tapering outer surface. Optionally, the at least one vent comprises a texturized surface different from the male coupler tapering outer surface. Optionally, the at least one vent extends along a linear path relative to the connection axis. Optionally, the at least one vent extends along a non-linear path relative to the connection axis. Optionally, the at least one vent extends along a helical path around the male coupler tapering outer surface. Optionally, the at least one vent comprises a length relative to the connection axis of between about 1.5 mm to 6.0 mm. Optionally, the at least one vent comprises a width relative to the connection axis of between about 0.125 mm to 5.0 mm. Optionally, the at least one vent comprises a depth from the male coupler tapering outer surface of between about 0.1 mm to 1.0 mm. Optionally, the male coupling further comprises a collar oriented about the connection axis, wherein the collar is configured to fasten to the enteral syringe female coupling. Optionally, the collar comprises threading. Optionally, the collar comprises a smooth inner surface that is configured to fasten to the enteral syringe female coupling with an interference fit. Optionally, the ISO 80369-3 compatible coupling is part of a syringe cap. Optionally, the ISO 80369-3 compatible coupling is part of a syringe-to-syringe coupler. Optionally, the ISO 80369-3 compatible coupling is part of oral administration coupler.

According to another aspect, the present disclosure relates to a male coupling oriented along a connection axis and configured for removable sealing engagement with a female coupling comprising a reservoir defined by a tapering inner surface extending between a narrowest closed end and a widest open end, the female coupler reservoir is configured to receive a volume of air, the male coupling comprising: a tapering outer surface extending between a widest fixed end and a narrowest distal tip, and a reservoir defined by an inner surface extending between a closed floor and an open distal end, the coupler tapering outer surface configured for removable sealing engagement with a female coupling tapering inner surface along the connection axis, the male coupler reservoir is configured to receive a volume of air; wherein, the male coupler tapering outer surface comprises at least one vent configured to permit an amount of the volume of air present in the male coupling reservoir and an amount of a volume of air present in a reservoir of the female coupling to escape during engagement between the male coupling and the female coupling, the at least one vent extending from the tapering outer surface distal tip towards the proximal end, the at least one vent is configured to provide a flow pathway between the male coupling tapering outer surface and the female coupling tapering inner surface to permit the volumes of air in the male and female couplings to escape therethrough.

Optionally, the male coupler tapering outer surface comprises a plurality of the vents. Optionally, the at least one vent comprises a surface configured to be removed from engagement with the female coupling tapering inner surface during engagement between the male coupling and the female coupling. Optionally, the at least one vent comprises a groove recessed from the male coupler tapering outer surface. Optionally, the at least one vent comprises a texturized surface different from the male coupler tapering outer surface. Optionally, the at least one vent extends along a linear path relative to the connection axis. Optionally, the at least one vent extends along a non-linear path relative to the connection axis.

According to another aspect, the present disclosure relates to a method for permitting a volume of air to escape a releasably sealed reservoir, the method comprising: receiving a male coupling within a female coupling along a connection axis, the male coupling comprising: a tapering outer surface extending between a widest fixed end and a narrowest distal tip, and a reservoir defined by an inner surface extending between a proximal end and an open distal end, the female coupling comprising: a reservoir defined by a tapering inner surface extending between a narrowest closed end and a widest open end; engagably sealing the male coupling tapering outer surface with the female coupling tapering inner surface; and permitting a volume of air to escape from within the male coupling reservoir and the female coupling reservoir through at least one vent extending from the male coupling distal tip towards the male coupling fixed end.

These and other aspects, features and advantages of the invention will be understood with reference to the drawing figures and detailed description herein and will be realized by means of the various elements and combinations particularly pointed out in the appended claims. It is to be understood that both the foregoing general description and the following brief description of the drawings and detailed description of example embodiments are explanatory of example embodiments of the invention, and are not restrictive of the invention, as claimed.

BRIEF DESCRIPTION OF THE DRAWINGS

FIG. 1B is a side view of the example enteral syringe, plunger and tip cap assembly shown in FIG. 1.

DETAILED DESCRIPTION OF EXAMPLE EMBODIMENTS

The present invention may be understood more readily by reference to the following detailed description of example embodiments taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 20:
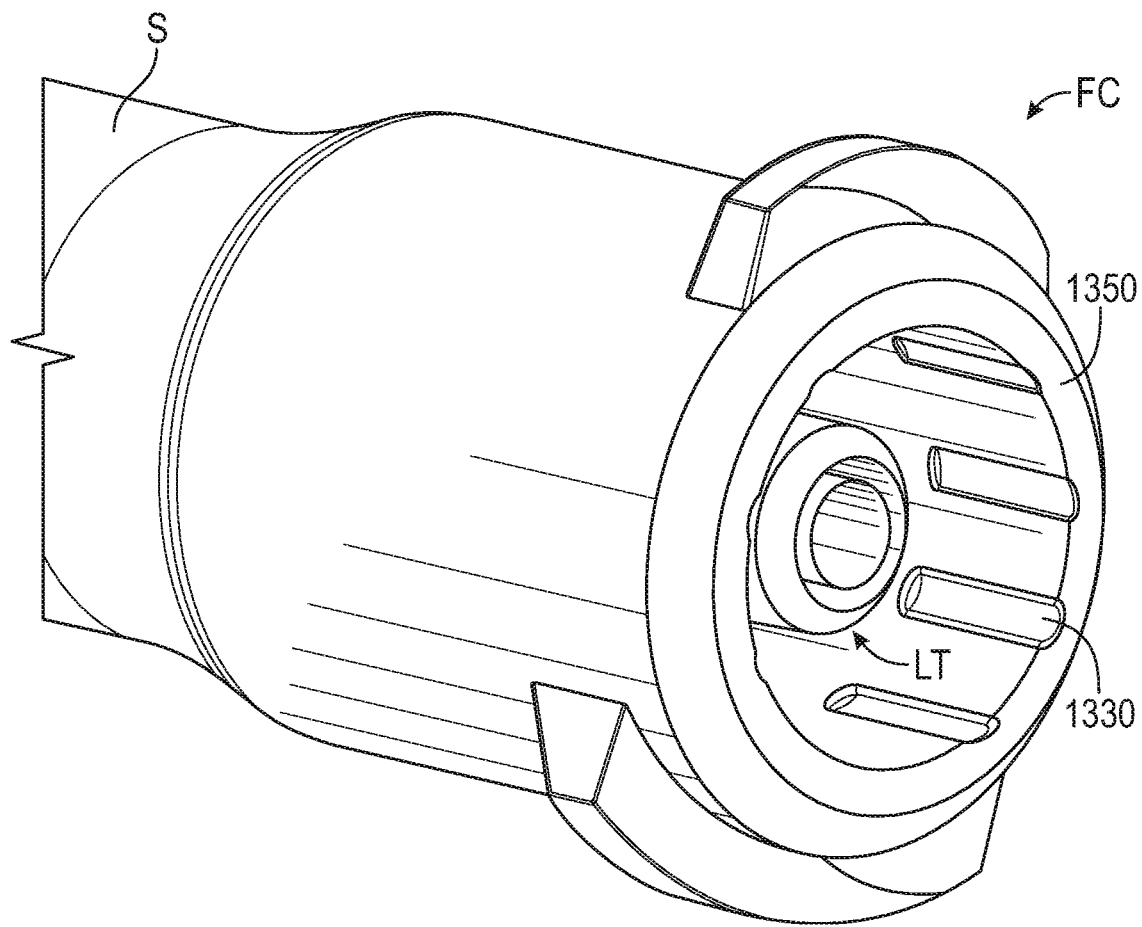
FIG. 20 is a sectional perspective view of a schematic diagram of a female coupling of an ISO 80369-3 compatible enteral syringe, according to another example embodiment of the present disclosure.
Figure 21:
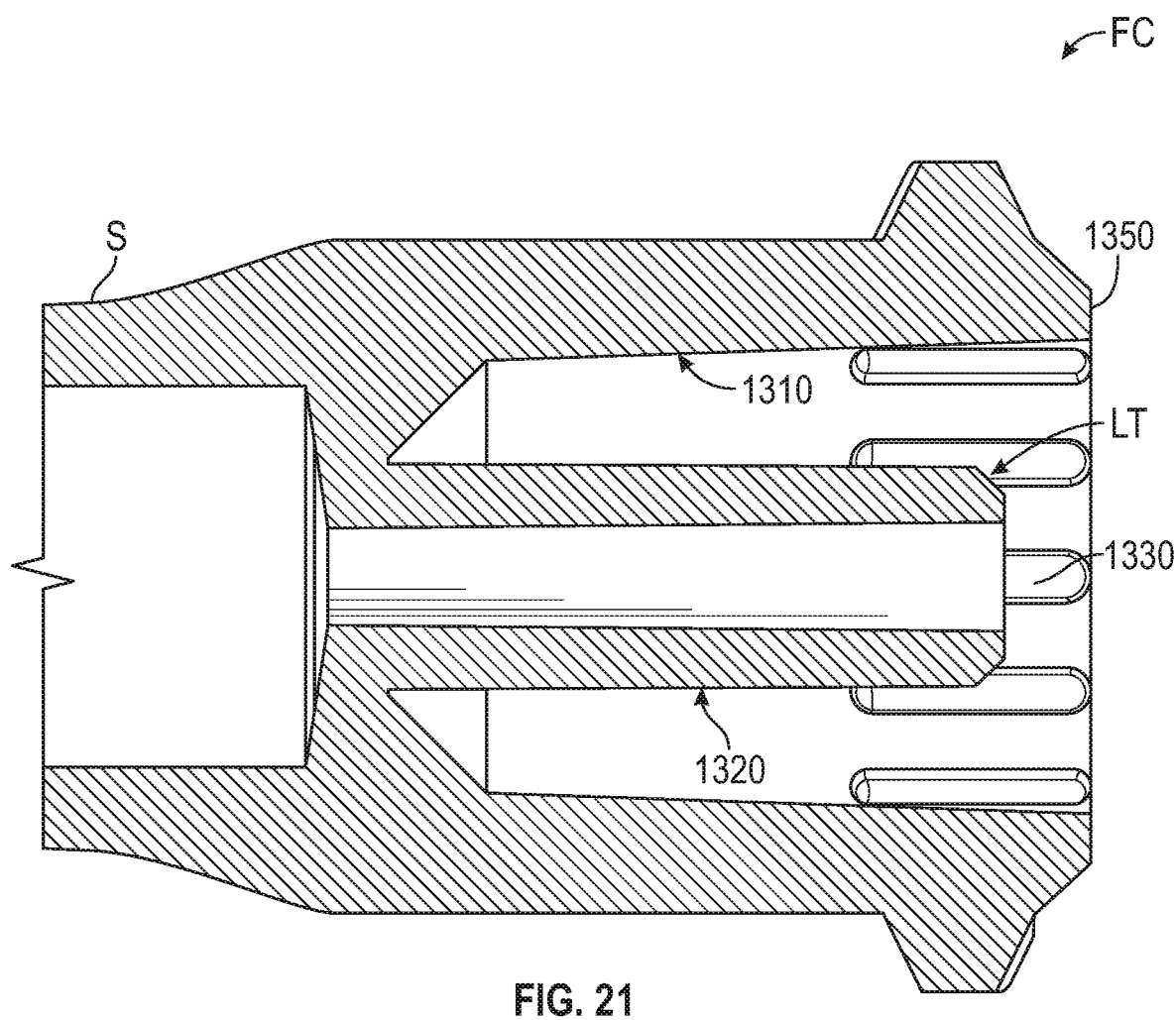
FIG. 21 is a sectional cross-sectional view of the female coupling shown in FIG. 20.

With reference now to the drawing figures, wherein like reference numbers represent corresponding parts throughout the several views, FIGS. 1A-7C show an example syringe S and tip cap 10 connected to the syringe S, and a plunger P translatably inserted within the syringe. In example embodiments, the syringe S and tip cap 10 have compatible couplings providing removable attachment, for example such as female and male couplings formatted for compatibility with the ISO 80369-3 or ENFit standard. The structure required by ISO 80369-3 or ENFit is an industry standard for enteral feeding connections. The general concepts of an ISO 80369-3 or ENFit compatible syringe are illustrated in FIGS. 20-21, further described below.

Figure 1A:
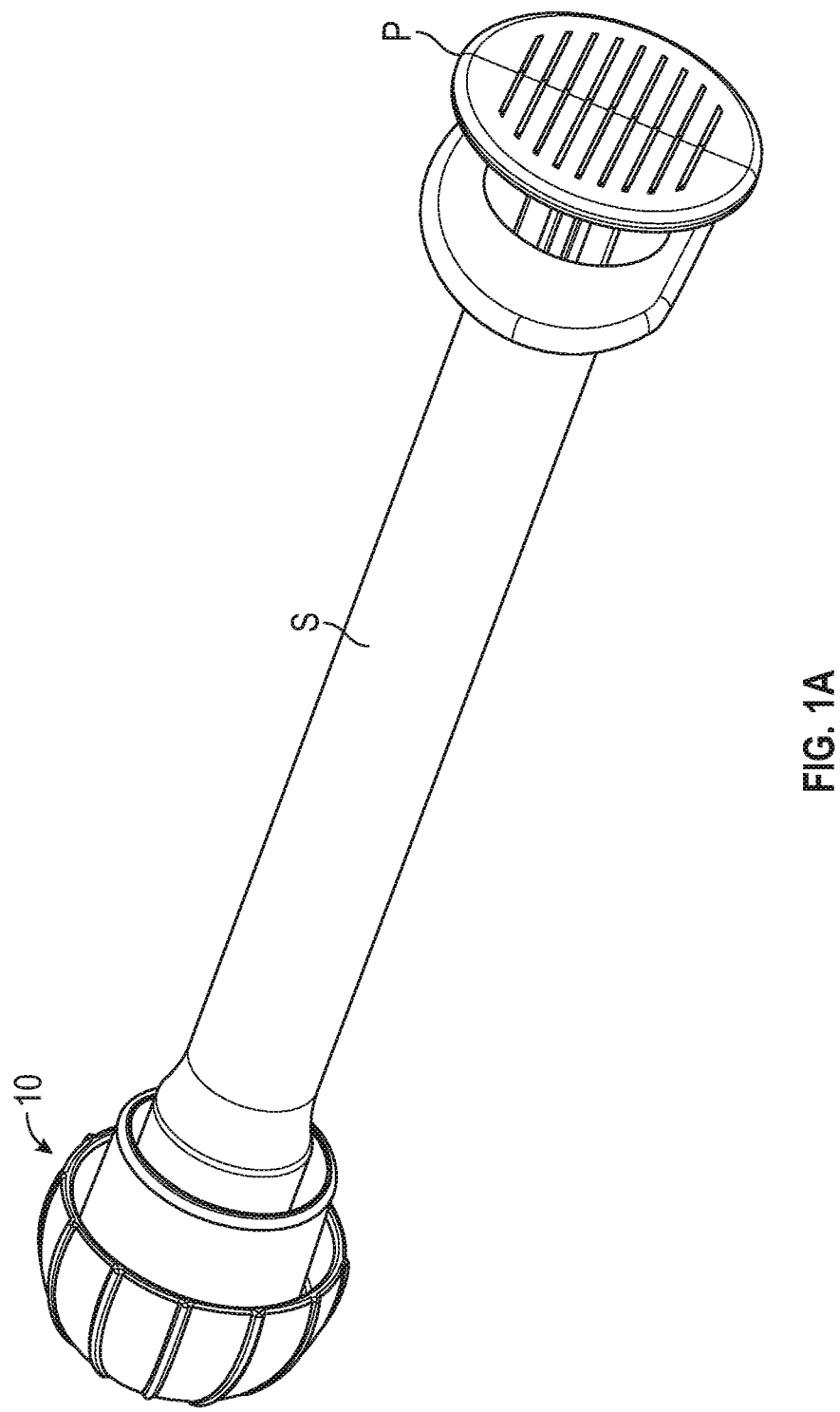
FIG. 1A is a perspective view of a schematic diagram of the general concepts of an example assembly including an ISO 80369-3 compatible enteral syringe, a plunger and a tip cap.
Figure 2:
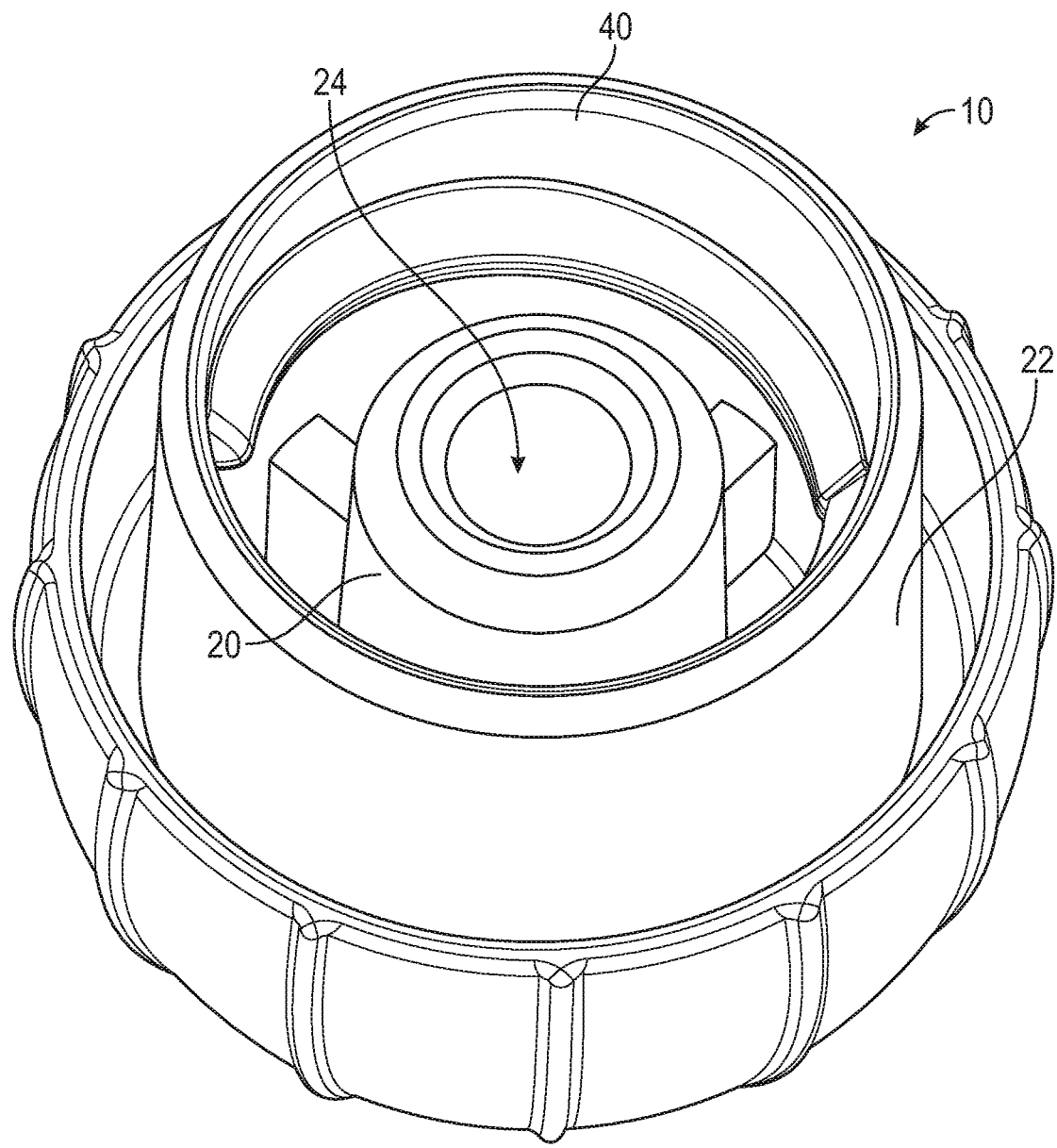
FIG. 2 is an isolated perspective top view of the tip cap shown in FIGS. 1A-1B.
Figure 3:
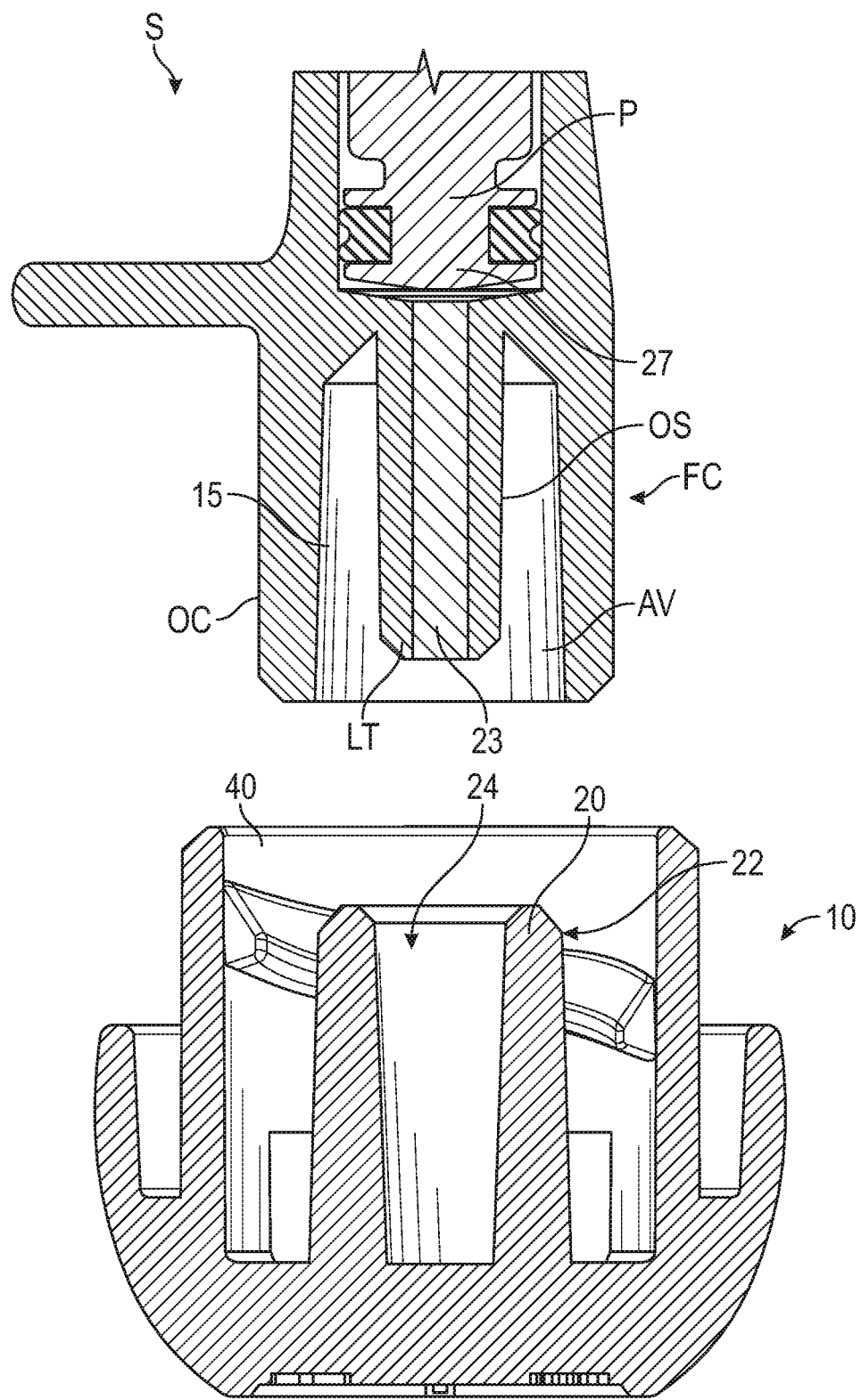
FIG. 3 is an isolated cross-sectional view of the tip cap and the syringe female coupling tip end shown in FIGS. 1A-1B, shown disengaged from each other.

As depicted in FIGS. 2-3, the tip cap 10 comprises a male connector or coupling 20 comprising an outer surface 22 for providing sealing engagement with a female coupling FC of the syringe S. While the tip cap 10 is illustrated for example, U.S. Published Patent Application Publication No. 2016/0067422 is also incorporated by reference herein and discloses additional example tip caps having male couplings formatted for compatibility with the ISO 80369-3 or ENFit standard. In example embodiments, the female coupling FC of the syringe S comprises a lumen extension tip LT. While the syringe S and lumen tip LT is illustrated for example, U.S. Published Patent Application Publication No. 2016/0317393 is incorporated by reference herein and discloses additional example syringes having compatible ISO 80369-3 or ENFit couplings and lumen extension tips.

As depicted in FIGS. 3-7C, attachment of the tip cap 10 with the female coupler FC of the syringe S causes the plunger P within the syringe S to be pushed or forced away from the female coupler and back within the syringe barrel, and in some cases causes fluid loss. As illustrated particularly by FIGS. 4-7C, as the female coupler FC is inserted within the tip cap 10 and begins to engage with the outer surface 22 of the male coupling 20 of the tip cap, a volume of ambient air becomes trapped within or between a recessed portion (or cavity) or reservoir 24 (defined within the male coupling 20) and an annular void AV of the female coupler (defined between the inner surface IS of the outer collar OC of the female coupler FC and an outer surface OS of the lumen extension tip LT), and further engagement therebetween causes the trapped volume of air to become compressed, thus increasing pressure.

The inner surface IS is tapered along a length, for example becoming increasingly wider with respect to the connection axis C from a narrowest position at a fixed or closed end or floor to a widest portion at a free distal end at the distal opening. The outer surface of the male coupling 20 is correspondingly and oppositely tapered, for example extending from a widest position at a closed end or floor of the cap 10 to a narrowest position at the free end at the distal opening to the reservoir 24.

As the outer surface 22 of the male coupling 20 and the inner surface IS of the female coupling FC frictionally and sealingly engage with each other, the volume of air within the reservoir 24 and within the annular void AV of the female coupling FC is trapped and becomes compressed with further engagement therebetween. In example embodiments, the pressure generated by the compressed air created within the reservoir 24 and annular void AV due to engagement of the female coupling FC and tip cap 10 is greater than the frictional engagement between the plunger P and the inner surface of the syringe barrel of the syringe S, which causes the plunger to be pushed or forced within the syringe barrel back or move rearwardly in a direction generally opposite and away from the female coupling FC (effectively equalizing the pressure). Thus, given that the outer surface 22 of the male coupling 20 and the inner surface IS of the female coupler FC are correspondingly tapered, and thus sealingly engage with each other (and prevent the trapped volume of air from passing through or escaping), the air that is trapped and compressed therein is forced between the engagement of the interior surface of the male coupling 20 defining the reservoir 24 and the outer surface OS of the lumen extension tip LT, such that the volume of trapped air moves within the conduit of the lumen extension tip LT and causes or forces the plunger P to be pushed back within the syringe barrel, as described.

Figure 4:
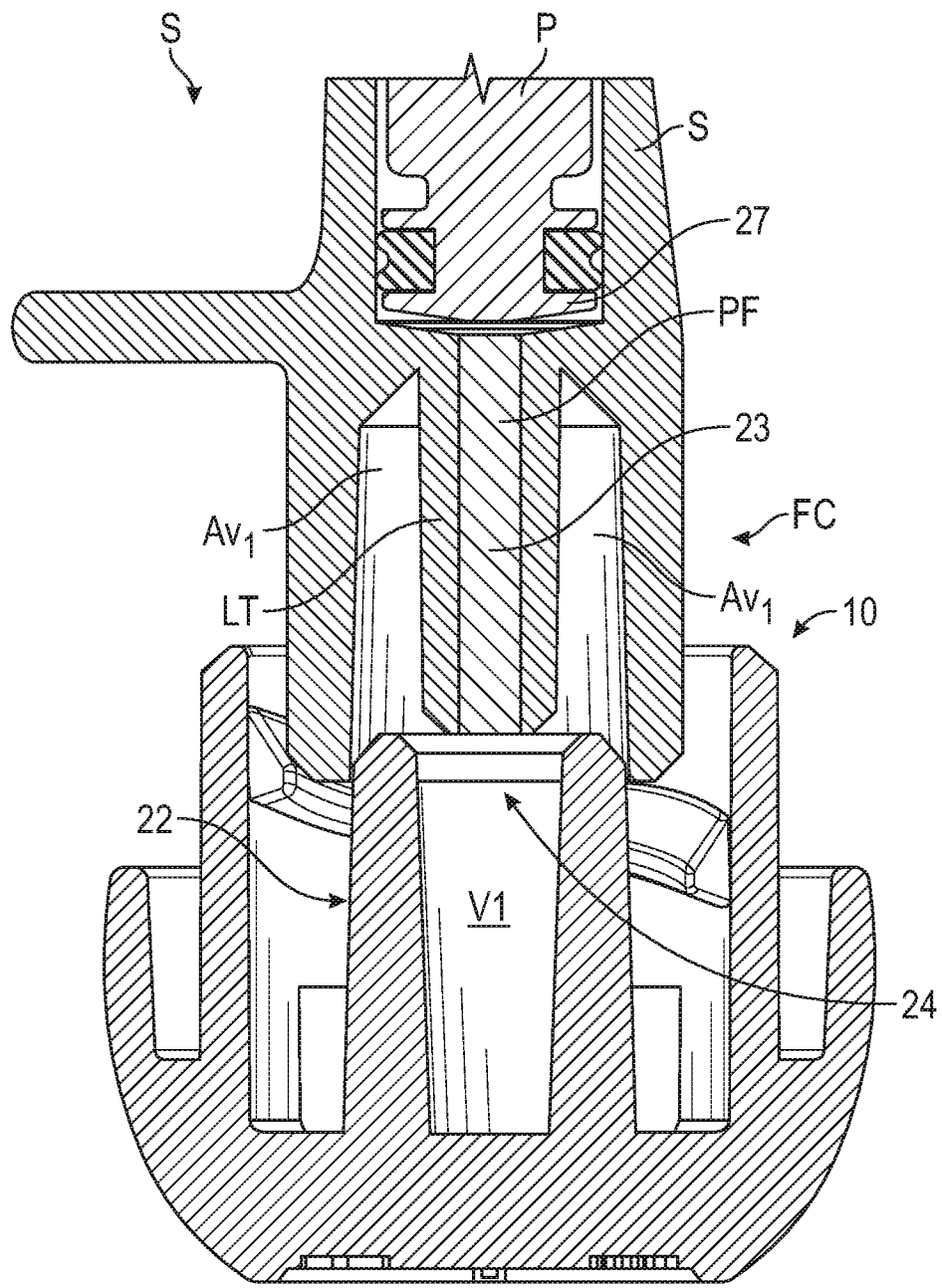
FIG. 4 is a cross sectional view of the tip cap and the syringe female coupling tip end shown in FIG. 3, shown in a first stage of engagement with each other.
Figure 5:
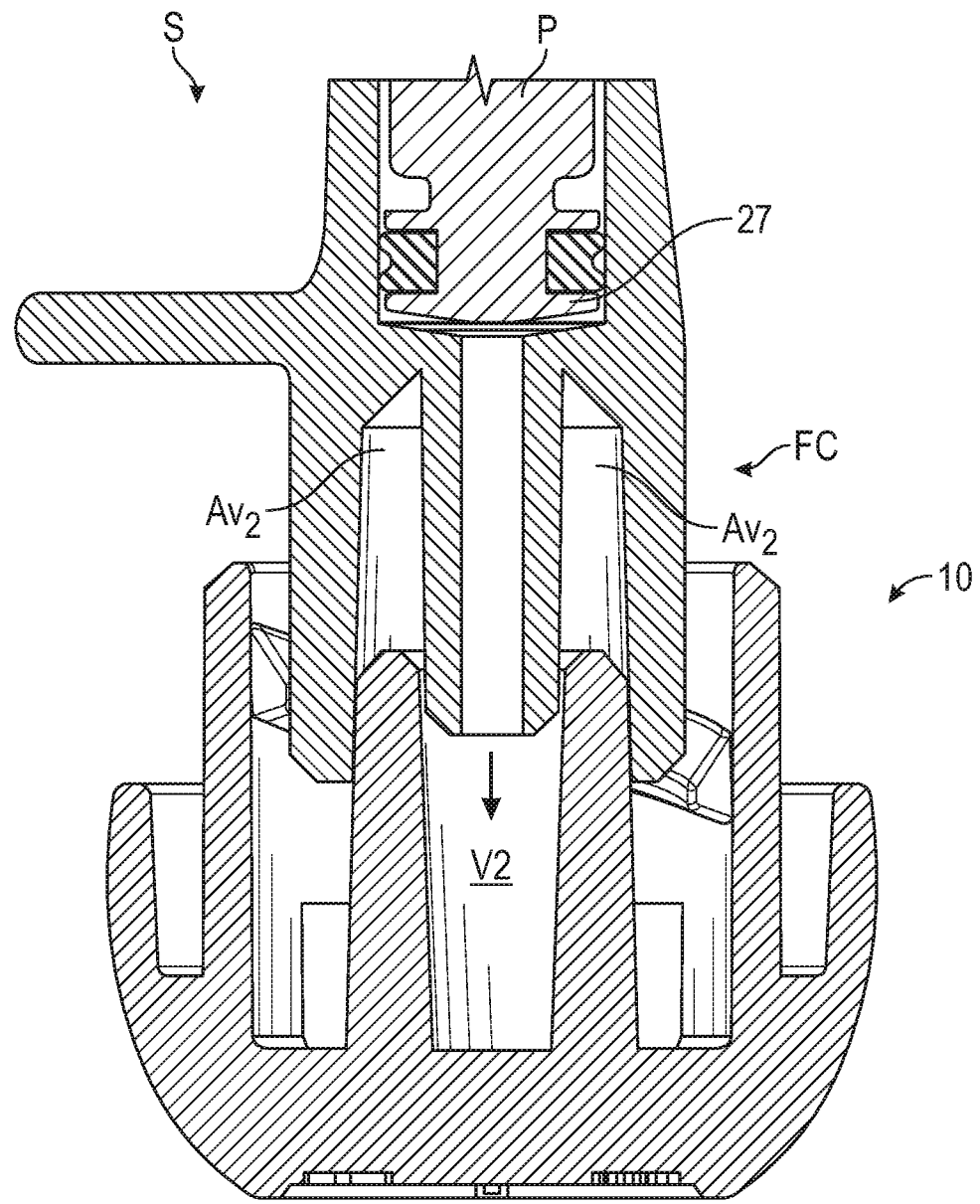
FIG. 5 is a cross sectional view of the tip cap and the syringe female coupling tip end shown in FIG. 3, shown in a second stage of engagement with each other.
Figure 6:
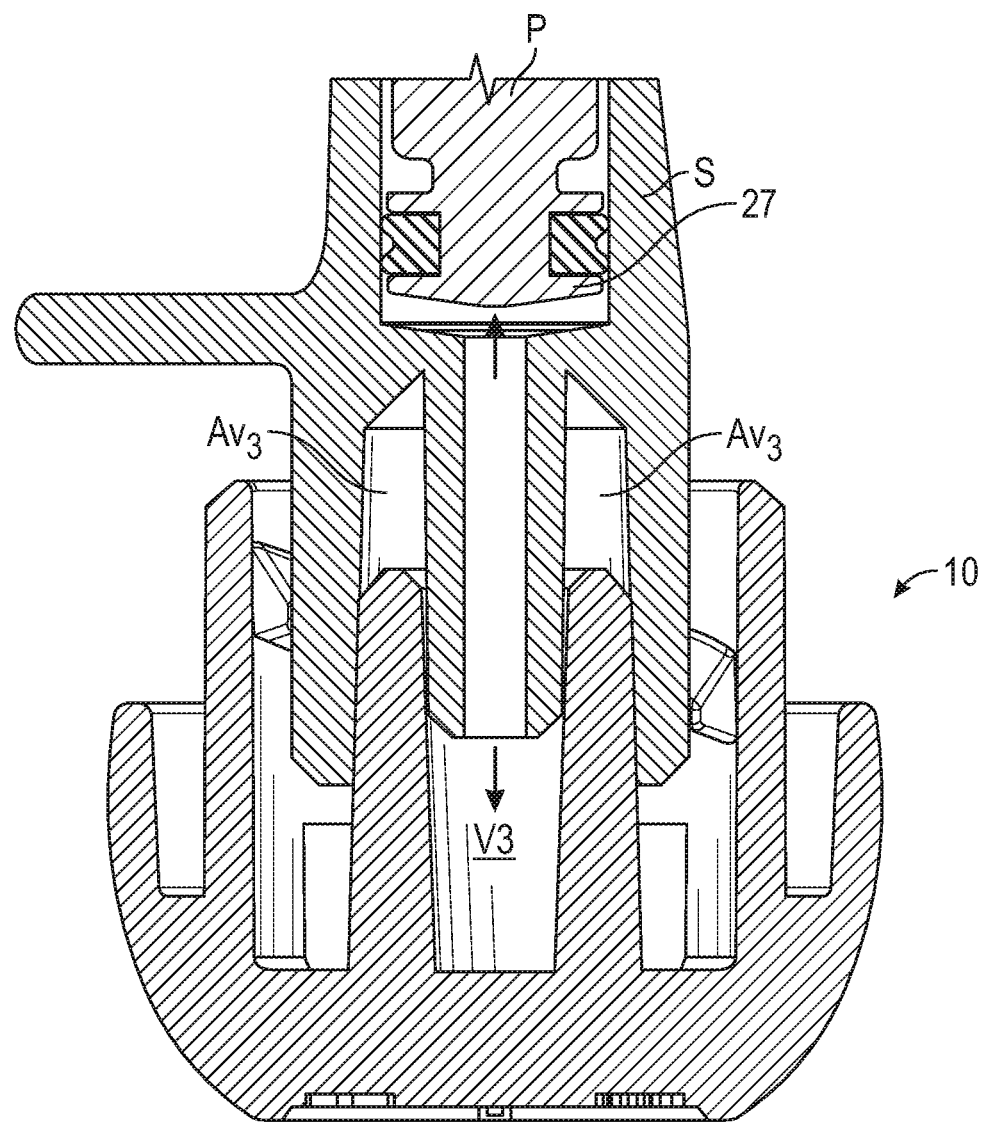
FIG. 6 is a cross sectional view of the tip cap and the syringe female coupling tip end shown in FIG. 3, shown in a third stage of engagement with each other.
Figure 7A:
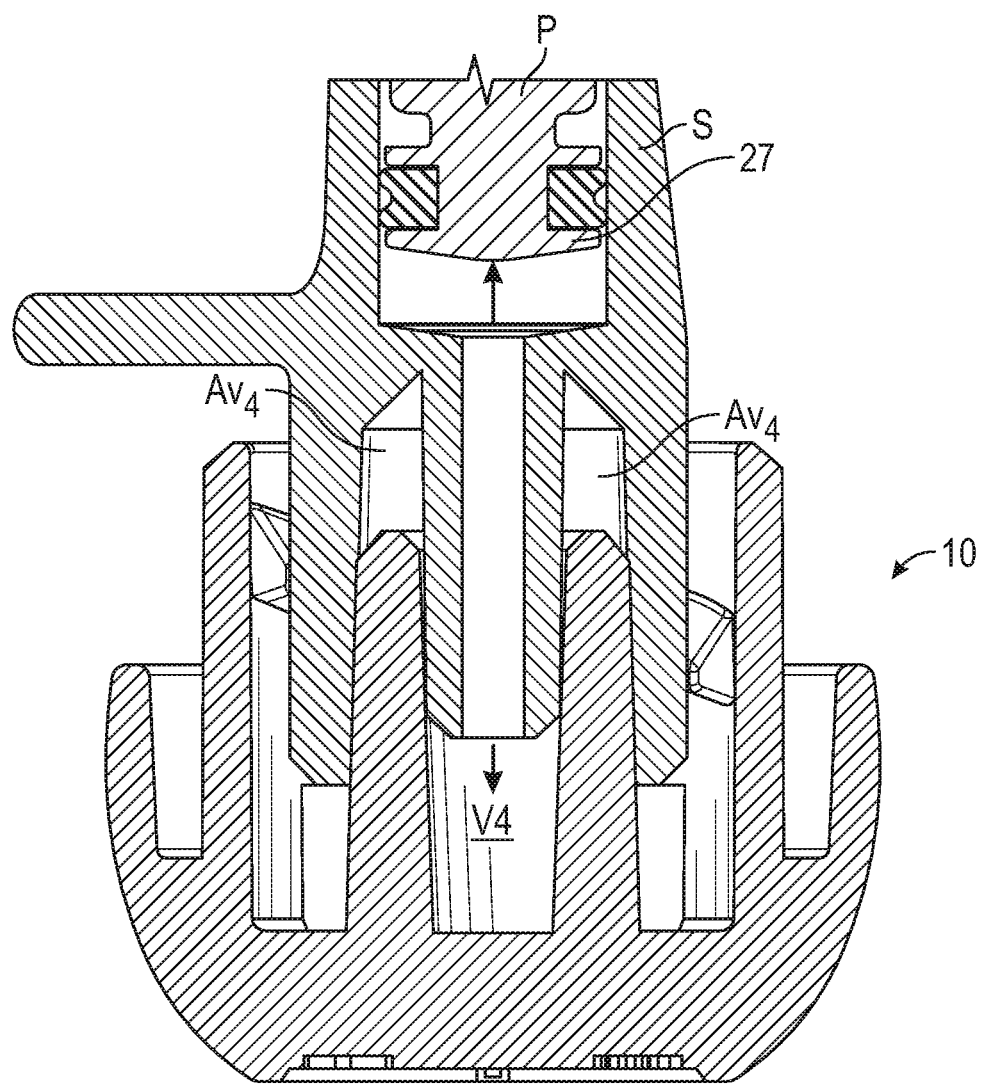
FIG. 7A is a cross sectional view of the tip cap and the syringe female coupling tip end shown in FIG. 3, shown in a fourth stage of engagement with each other.

FIGS. 4-7A illustrates an example sequence of the attachment and increased engagement of the female coupling FC of the syringe S and the tip cap 10. In FIG. 4, an example amount of ambient air is trapped within a volume $V_1$ is defined within the reservoir 24 and an annular volume $AV_1$ defined within the annular void AV, defined by the inner surface IS of the outer collar OC. As illustrated, as the syringe S and the tip cap 10 further interattach, the male coupling 20 increasingly occupies the annular void AV, and the lumen extension tip LT increasingly occupies the reservoir 24 defined by the male coupling 20, thus reducing the amount of free volume therein. As the engagement between the syringe S and the tip cap 10 increases, the amount of trapped air is thus compressed into a smaller volume $V_2$ that is defined within the reservoir 24 and a smaller annular volume $AV_2$ that is defined within the annular void AV, as illustrated in FIG. 5. As the engagement between the syringe S and the tip cap 10 increases further, the amount of trapped air is thus further compressed into an even smaller volume $V_3$ that is defined within the reservoir 24 and an annular volume $AV_3$ that is defined within the annular void AV, as illustrated in FIG. 6. As the engagement between the syringe S and the tip cap 10 further increases, the amount of trapped air is thus further compressed into an even smaller volume $V_4$ that is defined within the reservoir 24 and an annular volume $AV_4$ that is defined within the annular void AV, as illustrated in FIG. 7A.

As similarly described relative to the above, the volume of the annular void AV of the female coupling FC is reduced during engagement of the female coupling FC with the tip cap 10 (e.g., the male coupling 20 moving within the annular void AV). Thus, attachment of the female coupling FC with the tip cap 10 causes the voids within the couplings (e.g., reservoir 24 and annular void AV) to become occupied by the complementary engagement therebetween (e.g., male coupling 20 occupying at least a portion of the annular void AV of the female coupling FC and lumen extension tip LT occupying at least a portion of the reservoir 24, causing the volume of air therein to become trapped and compressed.

In example embodiments and as described above, an interior surface IS of the outer collar OC of the female coupling FC sealingly engages with the outer surface 22 of the male coupling 20. Thus, further engagement between the tip cap 10 and the female coupling FC causes compression of the air occupying the annular void AV and reservoir 24, resultingly increasing the amount of pressure generated by the trapped air. In example embodiments, the engagement between the outer surface 22 and the interior surface IS of the outer collar OC of the female coupler FC is airtight creating a seal such that even compressed air is prevented from passing therethrough. As such, when engaged, the compressed air that is trapped and compressed therein is not prevented from communicating with the conduit 23 (e.g., end opening) of the lumen extension tip LT (and the priming fluid PF contained therein), which ultimately exerts pressure or force on the priming fluid PF against the plunger head 27 and causes or forces the plunger P to be pushed back within the syringe barrel, as indicated by the arrow in FIGS. 6 and 7A.

Figure 7B:
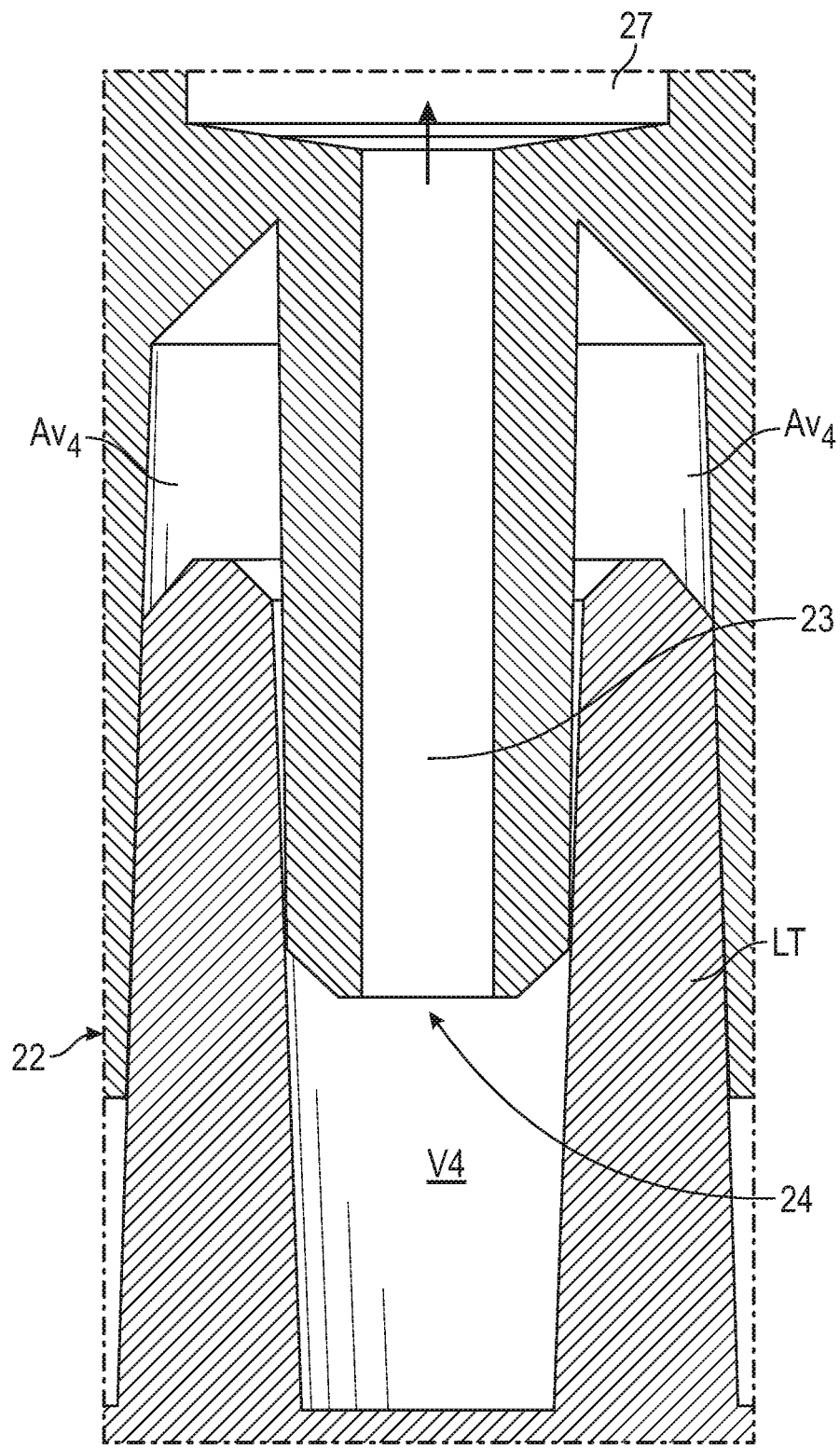
FIG. 7B is an enlarged sectional cross-sectional view of the engagement between the couplings of the tip cap and the syringe female coupling tip end shown in FIG. 7A.
Figure 7C:
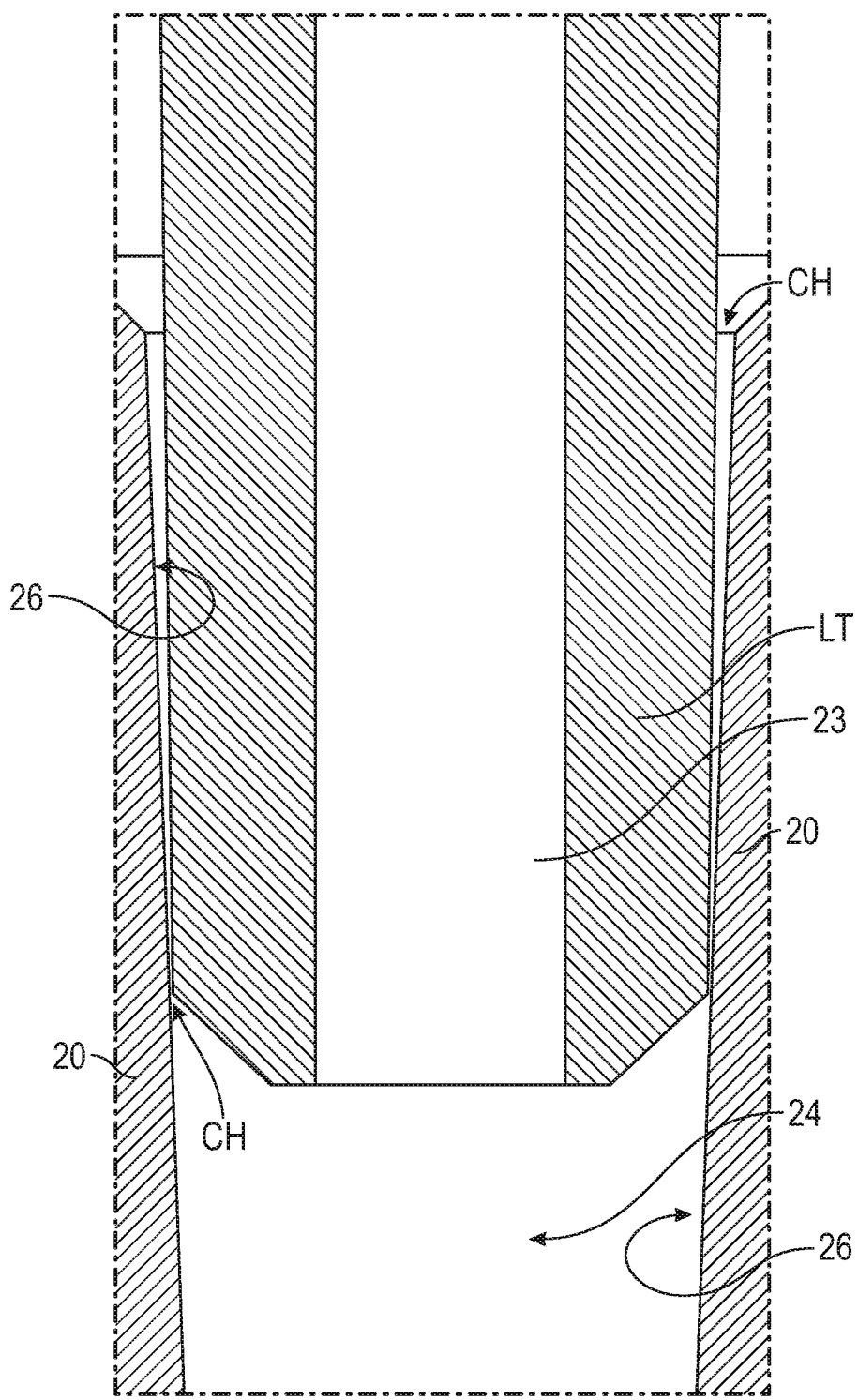
FIG. 7C is an enlarged sectional cross-sectional view of the engagement between the male conical connector syringe female coupling tip end and the male coupling of the tip cap shown in FIG. 7B.
Figure 8:
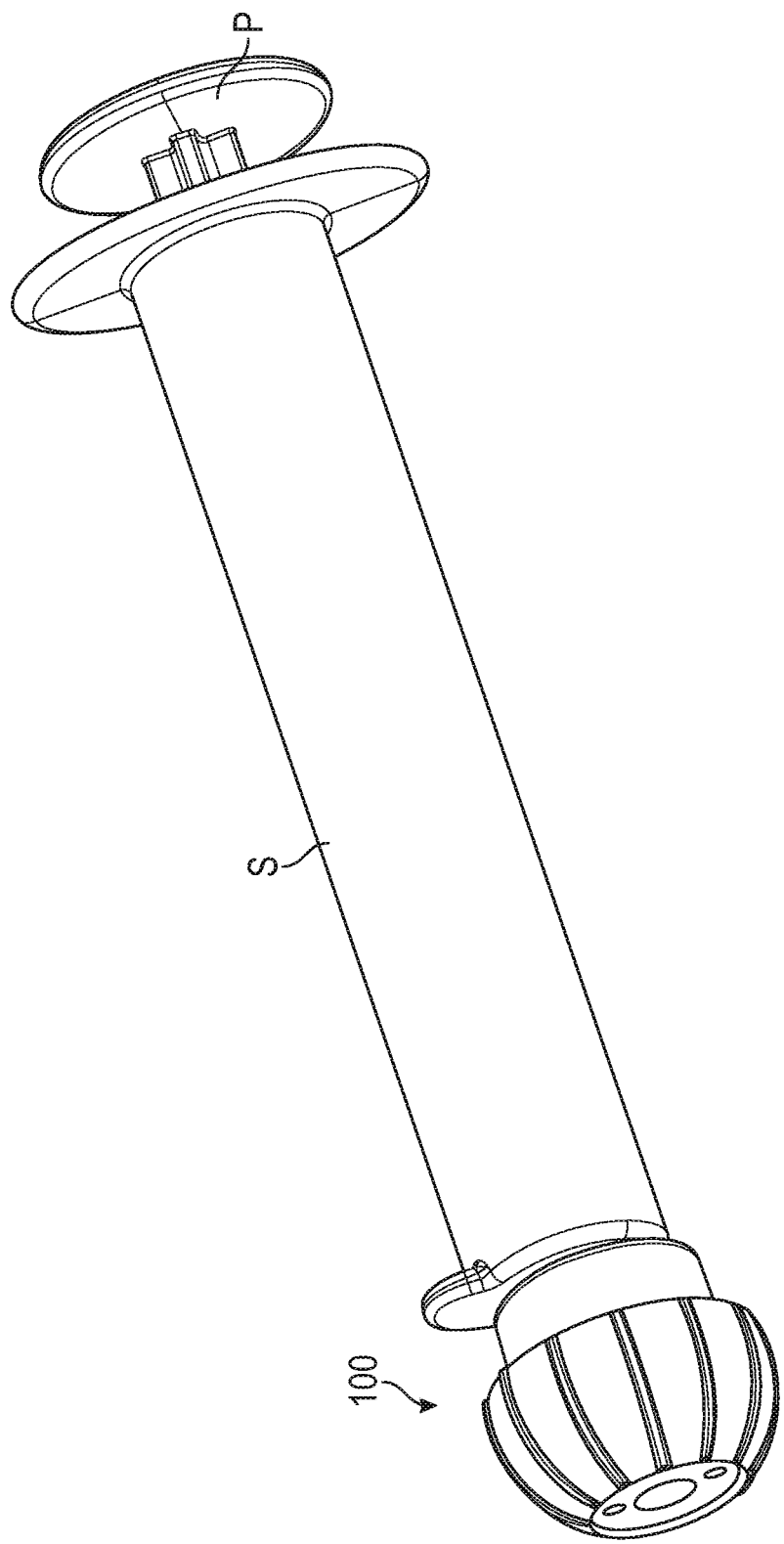
FIG. 8 is a perspective view of a schematic diagram of the general concepts of an example assembly including an ISO 80369-3 compatible enteral syringe, a plunger and a tip cap, according to an example embodiment of the present disclosure.
Figure 9:
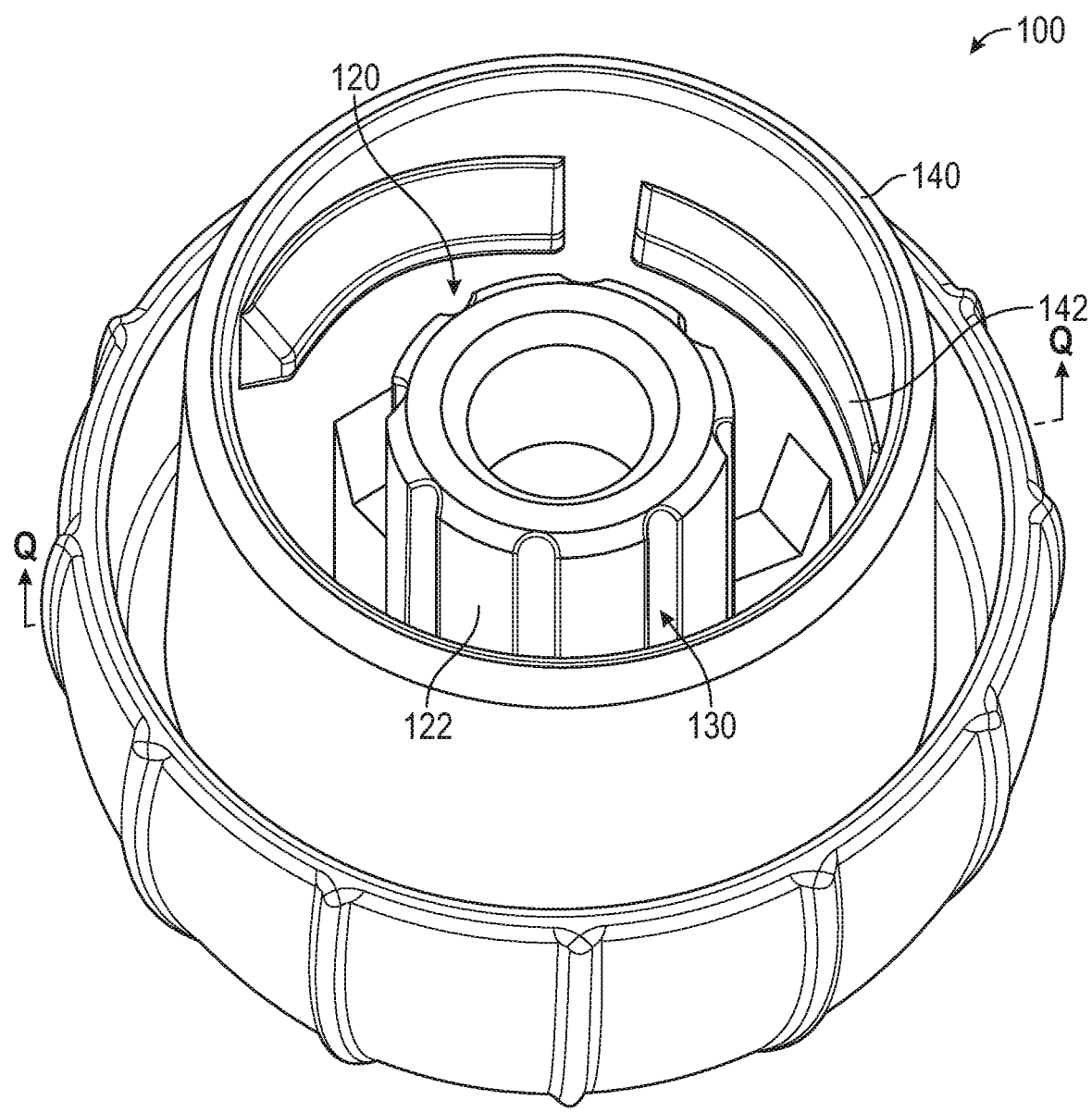
FIG. 9 is an isolated perspective top view of the tip cap shown in FIG. 8.
Figure 10:
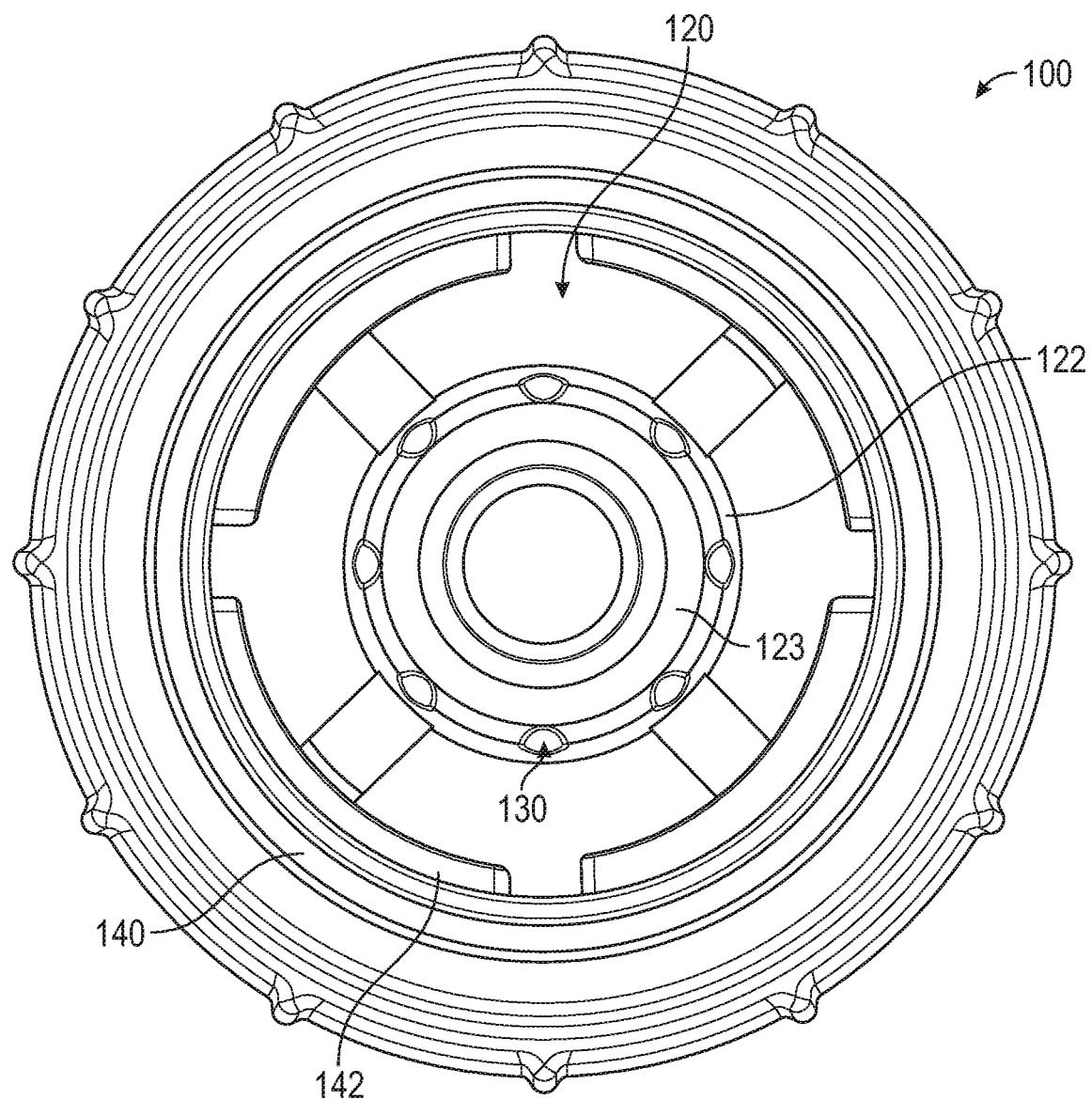
FIG. 10 is top view of the tip cap shown in FIG. 9.
Figure 11:
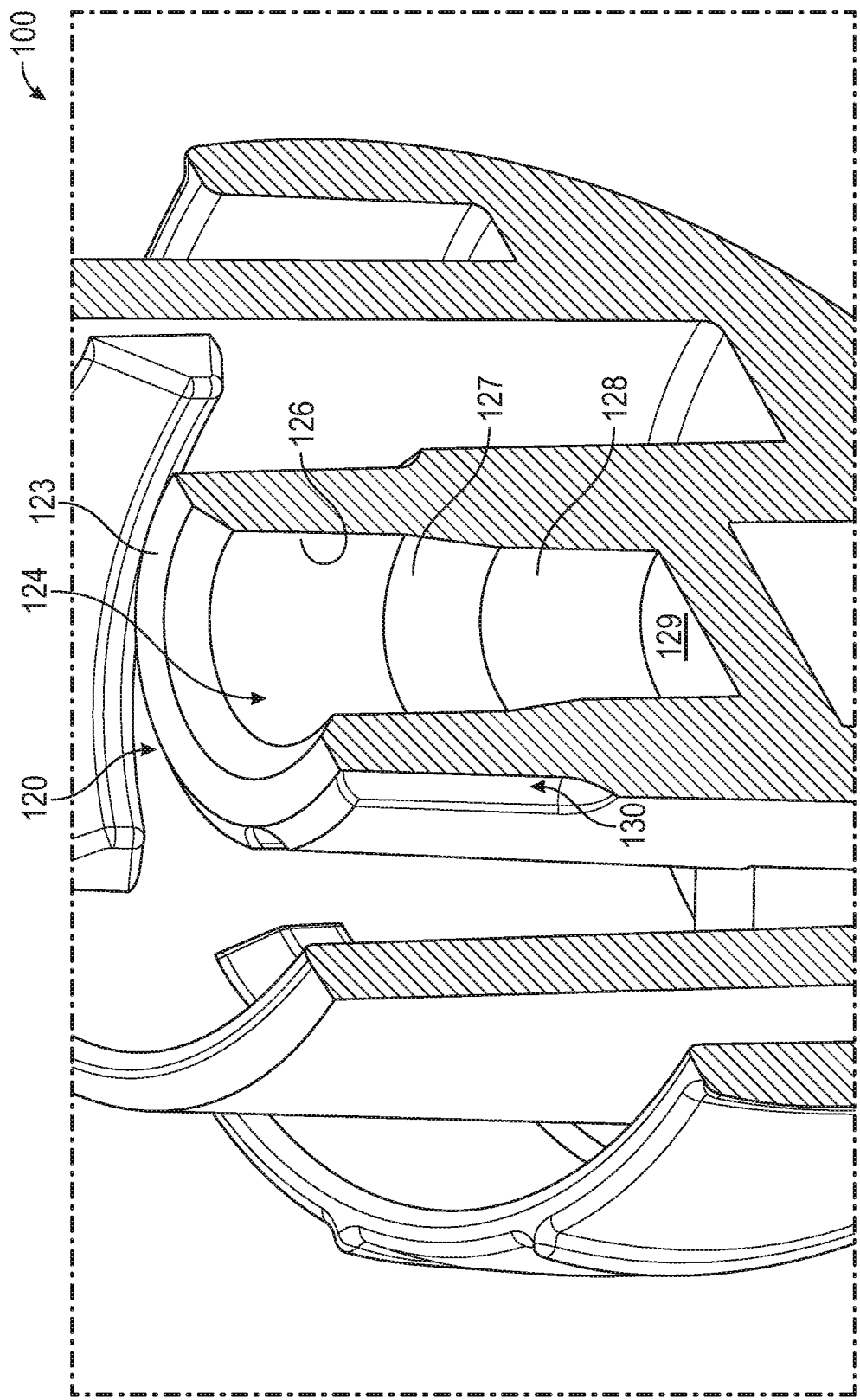
FIG. 11 is cross-sectional view of the tip cap shown in FIG. 8, viewed along sight line Q.
Figure 12:
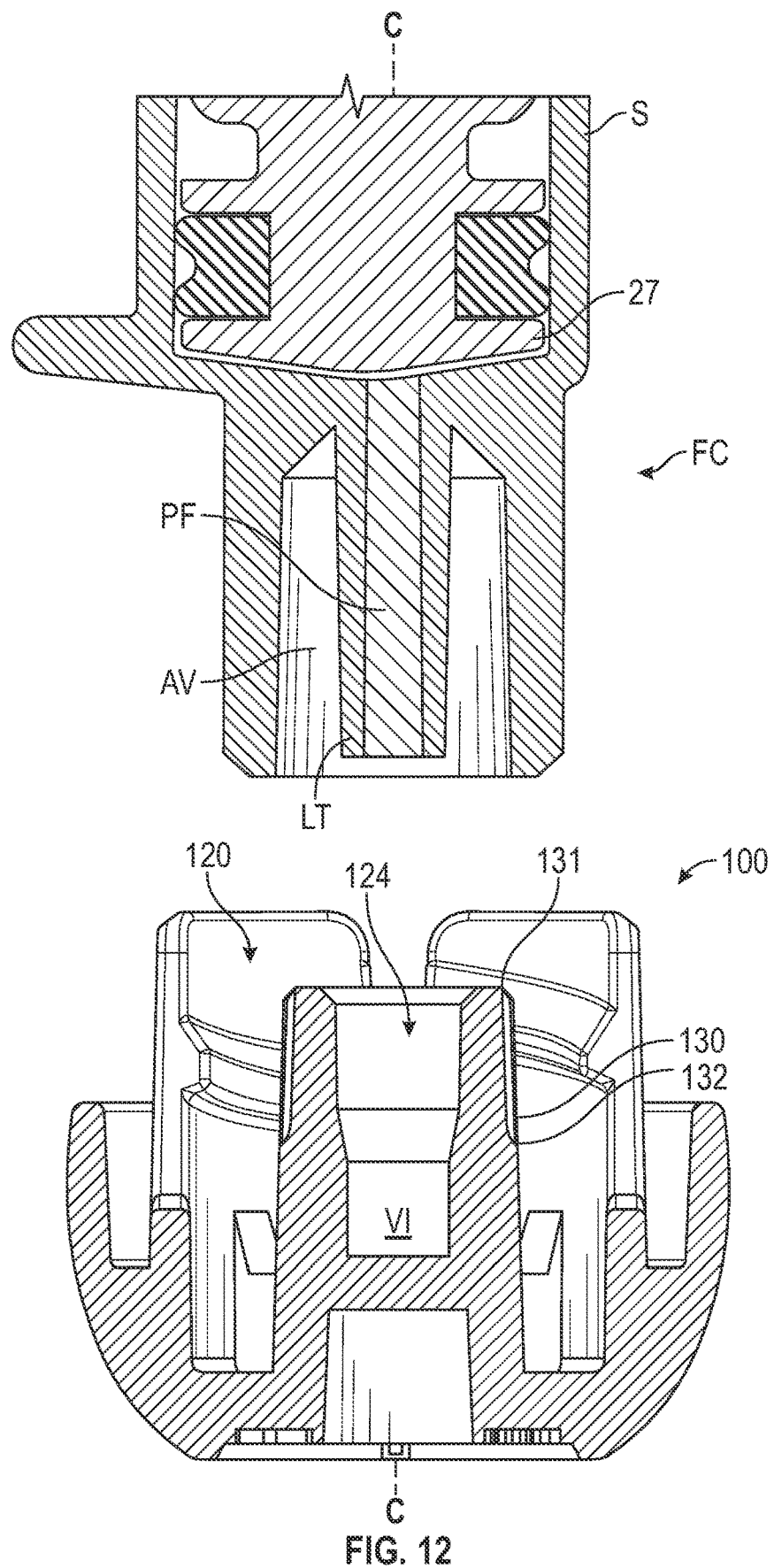
FIG. 12 is an isolated cross-sectional view of the tip cap and the syringe female coupling tip end shown in FIG. 8, shown disengaged from each other.

As depicted with enlarged detail in FIGS. 7B-C, at least one gap or channel CH (can also be called a passageway or pathway) is defined between an interior surface 26 of the male coupling 20 and the outer surface OS of the lumen extension tip LT, and thus, a communication path is defined therebetween such that the compressed air trapped in the annular void $AV_4$ being further occupied by the male coupling is allowed to communicate with the conduit 23 of the open end of the lumen extension tip LT and allow for the compressed air to cause or force pushback of the plunger P. According to one example embodiment, with the tip cap 10 sitting atop a supporting surface the female coupling FC of the syringe is moved in a first direction towards the male coupling 20, and wherein attachment therebetween causes the plunger P to be pushed back in a second direction generally opposite the first direction.

In example embodiments, the above-described plunger P pushback causes a discrepancy in the amount of fluid within the syringe S barrel, for example, such that the amount of fluid within the syringe prior to being capped with the tip cap 10 is not accurately the same amount of fluid within the syringe after attachment of the tip cap 10. Specifically, while the actual volume of fluid within the syringe S may be the same before and after being capped with the tip cap 10, the location of the plunger head 27 with respect to measurement lines on the syringe barrel is not the same. After being capped with the tip cap 10, the plunger head 27 is pushed backward into alignment with a measurement line on the syringe S to indicate that there is more fluid therein than there actually is. Furthermore, detachment of the tip cap 10 (after a previous attachment and plunger P pushback) can cause some residual fluid within the syringe barrel to remove itself from the syringe S (e.g., generally leaving from the conduit 23 of the lumen extension tip LT). And, in addition to fluid loss, the plunger P must be manipulated (e.g., depressed) to remove the air that entered the syringe barrel during the initial attachment, which can result in the plunger moving beyond the its original position prior to tip cap 10 attachment, for example, since some fluid can be lost during detachment.

Additionally, and without restricting the description above, FIGS. 3-7C show a sequence of operation of the female coupling FC and tip cap 10 attachment, and wherein the plunger P is pushed back due to air compressing within portions thereof and exerting pressure on the priming fluid within the conduit 23 of the lumen extension tip. As depicted, the plunger P is at a forward-most position within the syringe barrel. However, as is most generally the case, at least some amount of fluid is generally within the syringe barrel such that the plunger P is not at its forward-most position, but rather at a more rearward position within the syringe barrel. For example, since the tip cap 10 is normally at least initially attached to the female coupling FC after the syringe barrel is filled with a desired quantity of fluid (and the lumen extension tip primed with fluid PF), the plunger P will generally be at least somewhat offset from the forwardmost position. Thus, push back of the plunger 23 can occur regardless of its position when the tip cap 10 is attached to the female coupling FC. According to one example embodiment, for example wherein the syringe comprises a volume of about 1 mL and is filled such that the plunger P aligns with the 0.4 mL mark on the barrel's graduations, attachment of the tip cap 10 causes the plunger to push back and align with the 0.45 mL graduation mark, leading the clinician (the one who filled the syringe or another one who may go and administer the fluid) to believe that the dose is either inaccurate or that it has been altered or tampered with. The plunger pushing back can cause the syringe dose to be misread, can cause dosing accuracy concerns, can cause unwanted air/drug interactions, and an unwanted air bubble is a nuisance to users.

FIGS. 8-19 show a tip cap 100 according to an example embodiment of the present disclosure. As depicted, the tip cap 100 is generally similar to the tip cap 10 as described above and comprises a male coupling 120 and a threaded collar 140 comprising internal threads 142 for complementary engagement with threads or lugs of the female coupling FC of the syringe S. Similarly to the example described above, U.S. Published Patent Application Publication No. 2016/0067422 is incorporated by reference herein and discloses a plurality of tip cap designs having male couplings formatted according to the ENFit ISO 80369-3 standard. Optionally, according to additional example embodiments of the present invention, the tip cap can comprise a threaded collar with a plurality of clips for example as illustrated and described in FIGS. 8-29 of U.S. Patent Application 62/620, 576 filed on Jan. 23, 2018 which is incorporated by reference for all purposes, a partially threaded collar (with or without clips), a thread-less friction fit design, or other desirable threaded or thread-less designs. For example, as described in FIG. 19, the tip cap can be configured for a friction-fit attachment with the female coupling FC.

In example embodiments, the male coupling 120 comprises an outer surface 122, an end surface 123, and a reservoir 124 defined within the coupling 120. In example embodiments, the male coupling 120 is formatted for compatibility with the ISO 80369-3 or ENFit design standard. The reservoir 124 is defined by a geometry that comprises an interior surface comprising a first interior (mouth) section 126, a transition section 127, a second interior (sealing engagement) section 128, and a floor section 129. As illustrated, the first interior section 126 is wider or has a greater area than the second interior section 128, with the transition section 126 providing a tapered surface extending therebetween.

Figure 15:
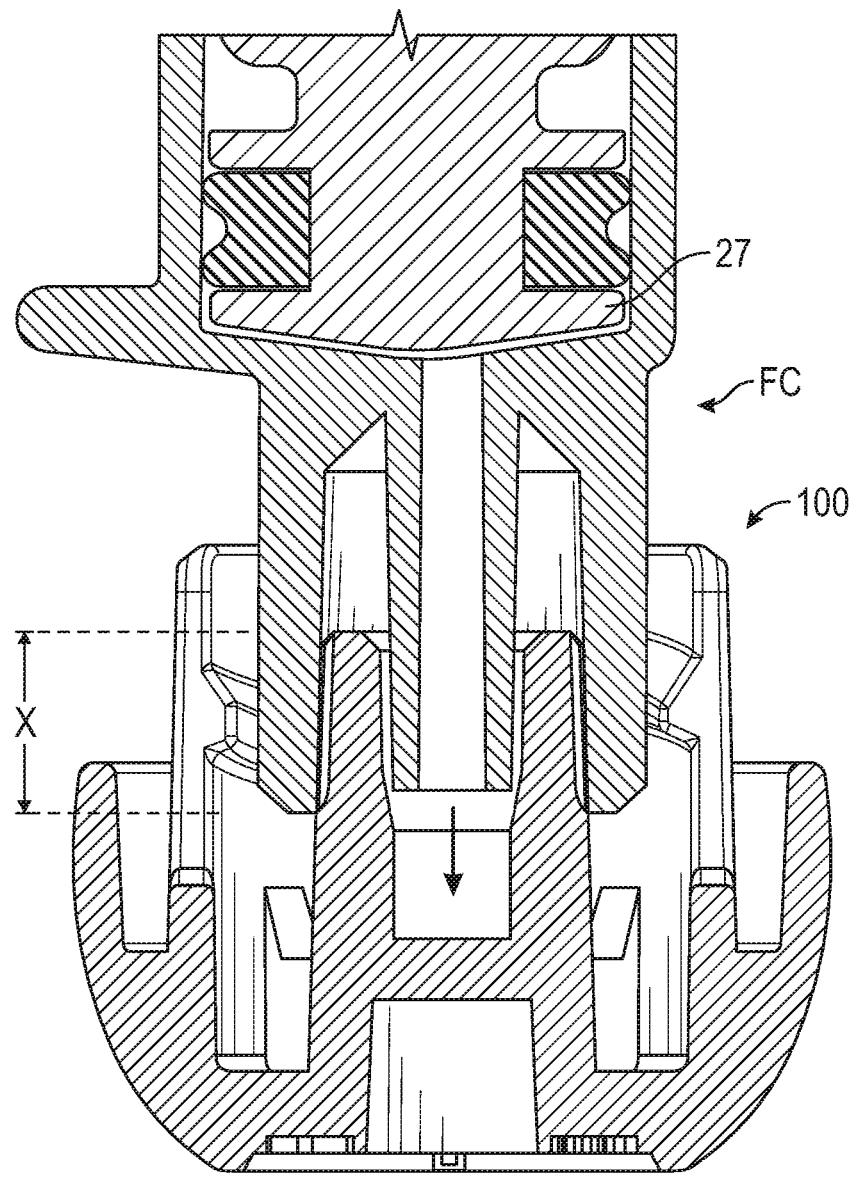
FIG. 15 is a cross sectional view of the tip cap and the syringe female coupling tip end shown in FIG. 13, shown in a third stage of engagement with each other.

In example embodiments, the male coupling 120 further comprises at least one recessed slot or spline portion (or grooved vent path or vent) 130 that extends along the outer surface 122, relative to the connection axis C, from the end surface 123 towards an opposite end thereof. As illustrated in FIG. 15, the vent 130 comprises a length X of between about 1.5-6 millimeters, more preferably between about 2.5-5 millimeters, for example about 3.773 millimeters according to one example embodiment. This length is functionally important because, when using ISO 80369-3 compatible couplings, any length shorter than these described minimums will not allow for enough of the trapped volume of air to escape, as the inner surface IS of the female outer collar OC and the outer surface 122 of the male coupling 120 increasingly interengage. Similarly, a length greater than the above described maximum was determined to not adequately allow for a sealed engagement between the inner surface IS and the outer surface 122 concurrently with the engagement of the outer surface of the lumen extension tip LT and the inner surface of the reservoir 124.

In example embodiments, the vent 130 comprises a width of between about 0.125-5 millimeters, more preferably between about 0.25-2 millimeters, for example about 0.556 millimeters according to one example embodiment. In example embodiments, the vent 130 comprises a depth from the outer surface 122 of between about 0.1-1.0 millimeters, more preferably between about 0.25-0.7 millimeters, for example about 0.399 millimeters according to one example embodiment. This depth can reflect a diameter, such that the vent 130 can have a generally semi-circumferential geometry. As depicted, the vent 130 can have a top opening 131 reflecting the maximum depth at the top surface 123 and extend to a closed distal end 132 away from the top surface 123, such that the depth from the outer surface 122 is zero.

The illustrated male coupling 120 comprises a circular array of eight equally spaced apart vents 130. Optionally, more or less than eight vents are within the scope of the invention. In other example embodiments, the vents 130 can comprise irregular spacing therebetween and can be preferably sized and shaped as desired. For example, the depicted vents 130 generally extend along a linear path along an orientation angle distinct from a connection axis C between the syringe S and the tip cap 100. However, in other example embodiments, the vent paths 130 can extend along a non-linear path or for example, a helical path or spline.

FIGS. 12-18 show a sequence of operation of attachment of the tip cap 100 to the female coupling FC of the syringe S. As depicted, the vents 130 preferably allow for a substantial amount of air to escape the reservoir 124 (and annular void AV of the female coupling FC) prior to sealing engagement between the male coupling 120 and the female coupling FC, for example, such that the air that is trapped within the reservoir 124 after sealing engagement (between the male coupling 120 and the female coupling FC) is incapable of being pressurized to the extent of overcoming the frictional engagement of the plunger P with the syringe barrel. Thus, while trapping some air within the reservoir 124 (and annular void AV) during attachment of the male coupling 120 with the female coupling FC, the trapped air (ultimately pressurized when fully attached) is minimal and insufficient to cause the plunger to push back, which is distinct from the embodiment described above in FIGS. 1-7. As such, in addition to no plunger pushback, and a more accurate reading with respect to the measurement lines on the syringe barrel, the likelihood of fluid loss is substantially zero if not entirely negligible.

Figure 13:
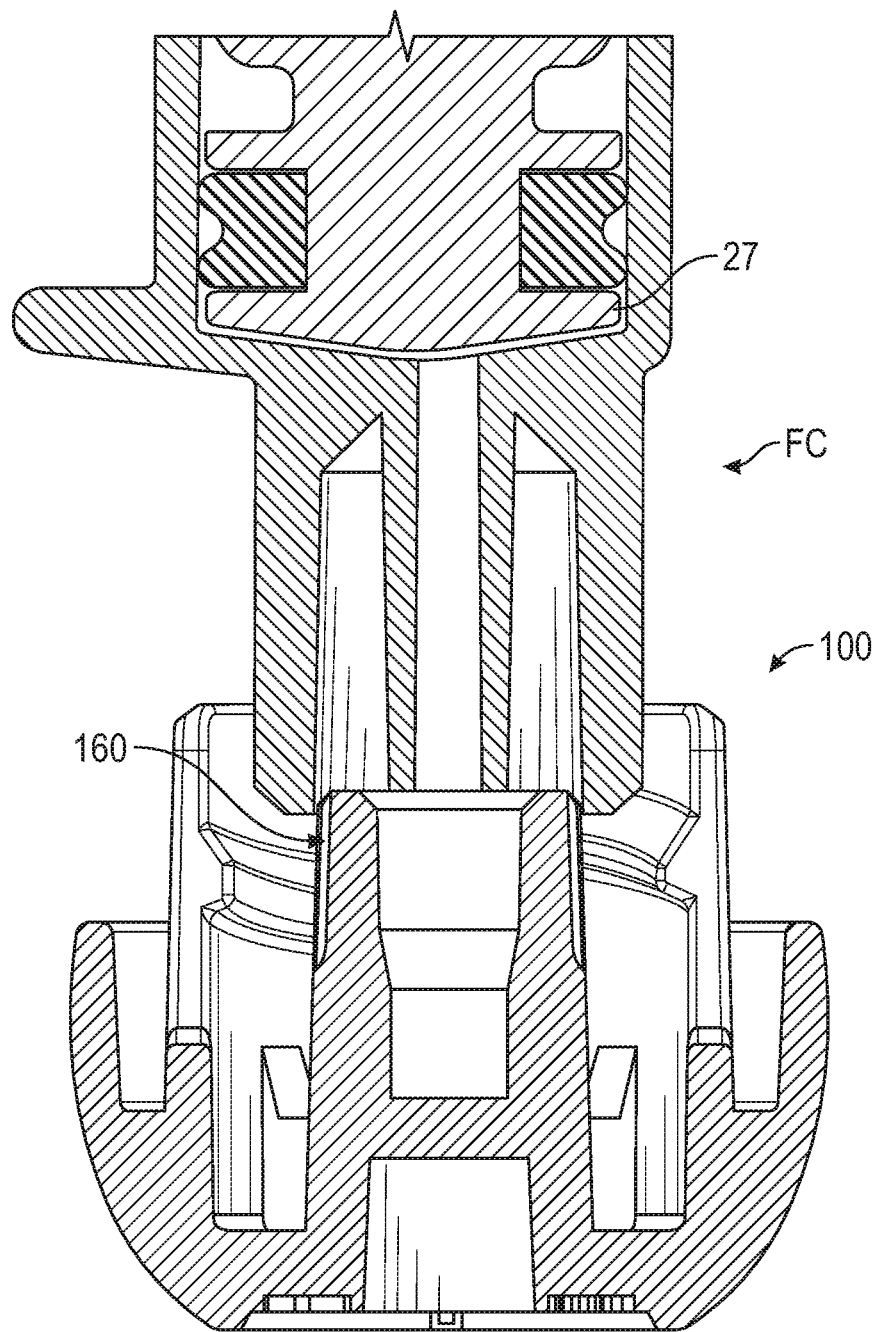
FIG. 13 is a cross sectional view of the tip cap and the syringe female coupling tip end shown in FIG. 12, shown in a first stage of engagement with each other.
Figure 14:
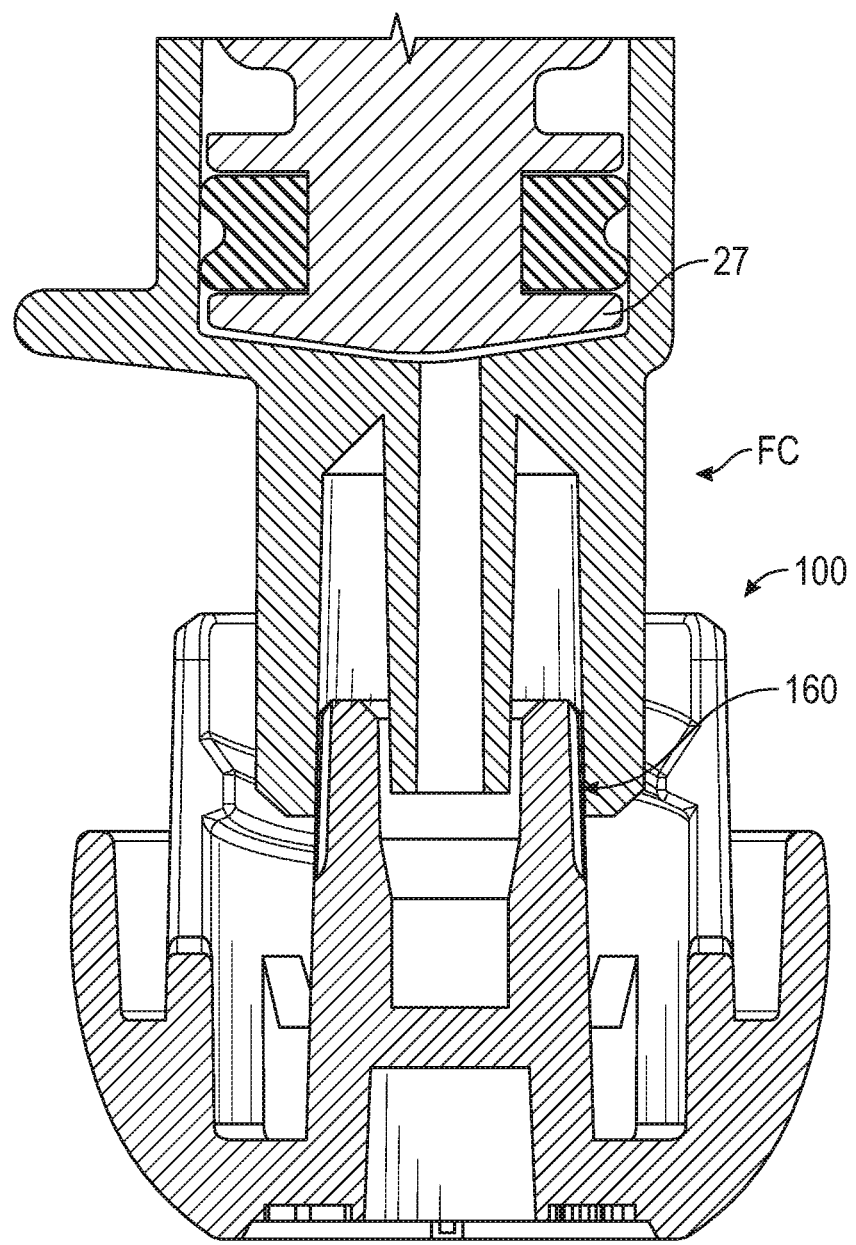
FIG. 14 is a cross sectional view of the tip cap and the syringe female coupling tip end shown in FIG. 12, shown in a second stage of engagement with each other.
Figure 16:
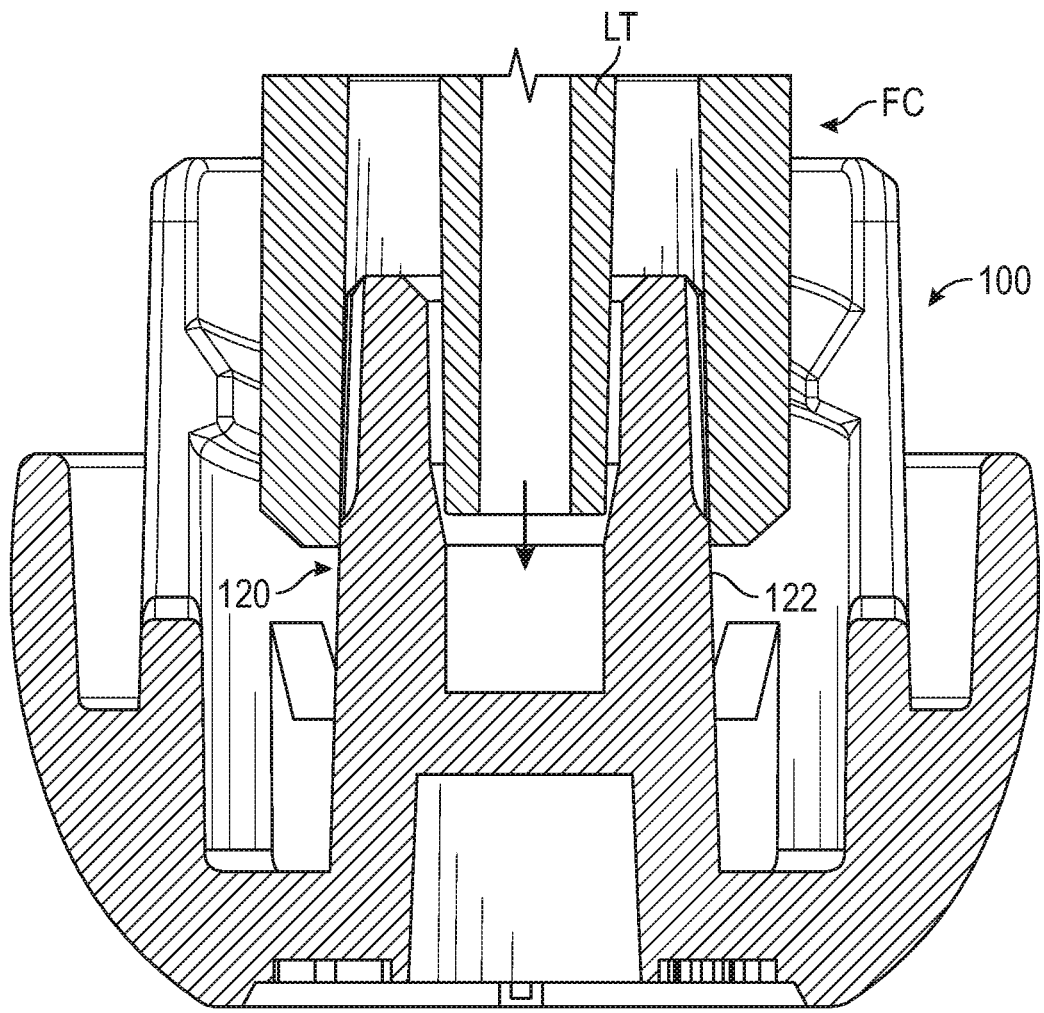
FIG. 16 is an enlarged sectional cross-sectional view of the tip cap and the syringe female coupling tip end shown in FIG. 15.
Figure 17:
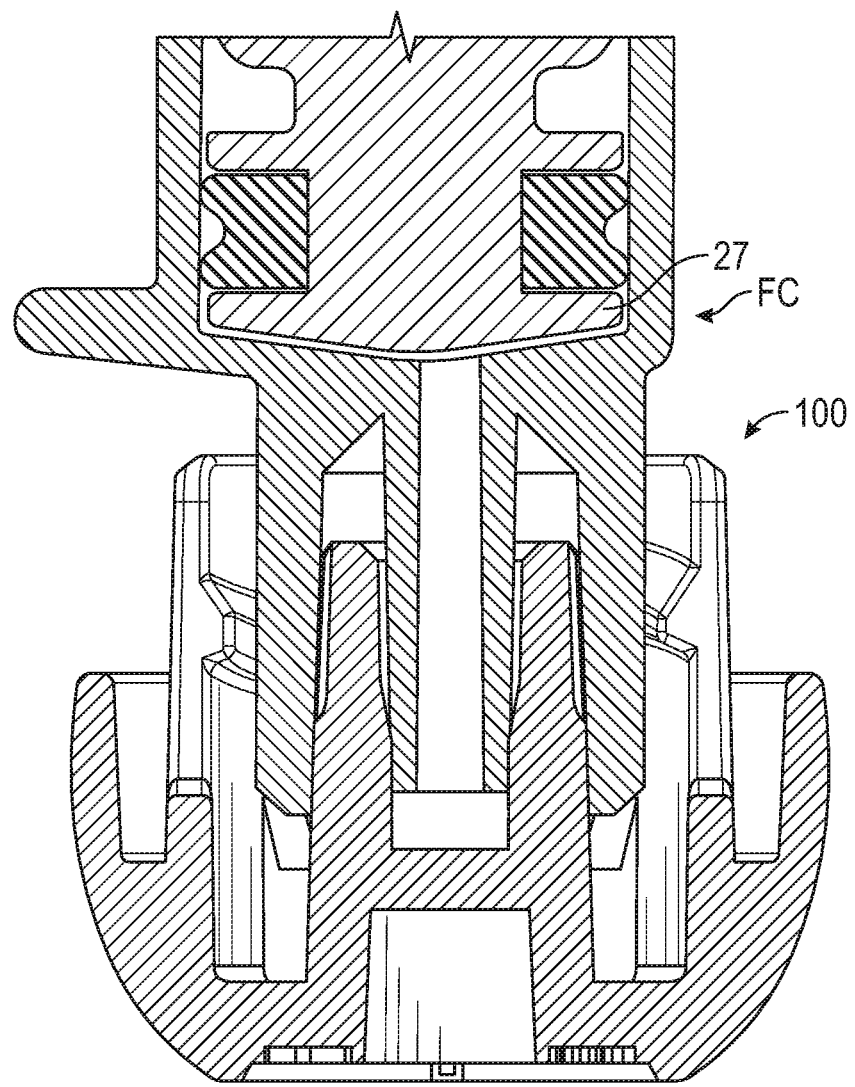
FIG. 17 is a cross sectional view of the tip cap and the syringe female coupling tip end shown in FIG. 13, shown in a fourth stage of engagement with each other.
Figure 18:
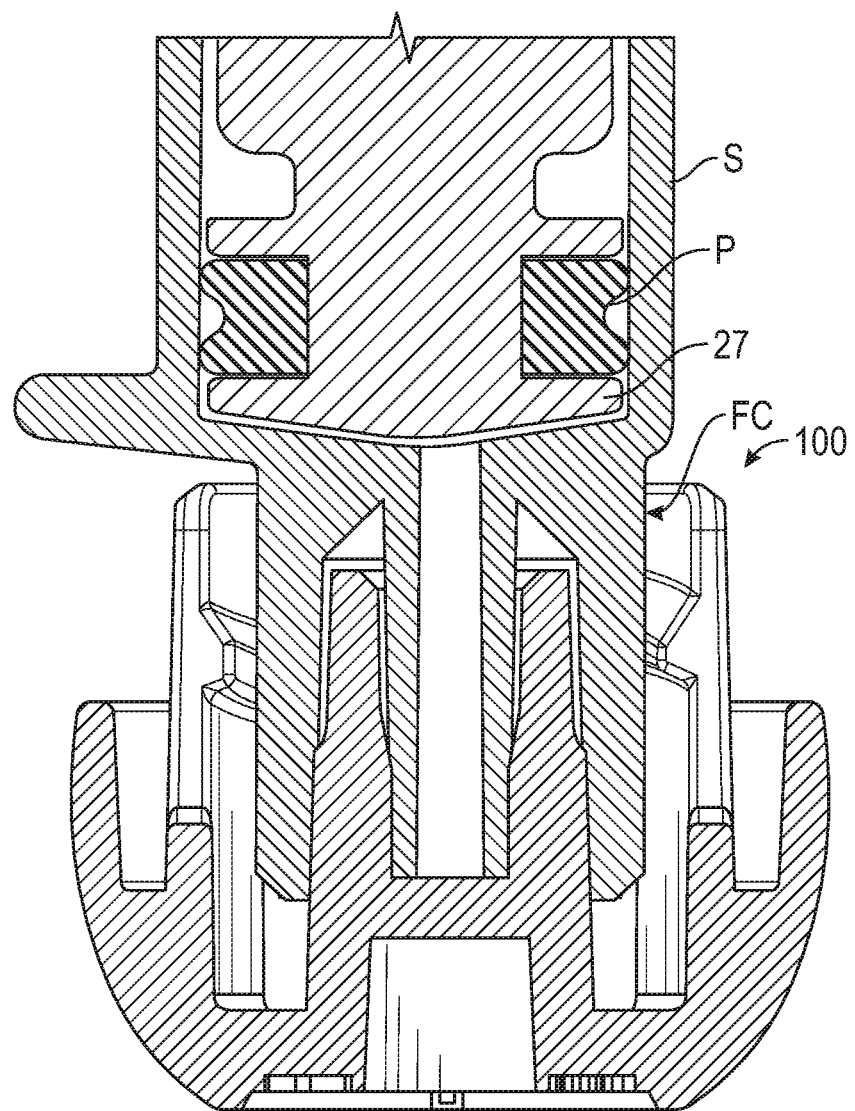
FIG. 18 is a cross sectional view of the tip cap and the syringe female coupling tip end shown in FIG. 13, shown in complete engagement with each other.

FIGS. 13-14 show a step in the sequence of operation of the attachment of the tip cap 100 with the female coupling FC. As shown, the tip cap 100 and the female coupling FC can engage one another up to the length X of the vent 130, (e.g., overlap between components) while still allowing for air to escape and prior to sealing engagement therebetween. For example, as shown in FIGS. 13-14, just prior to sealing engagement, a pathway 160 for venting is still provided between the vents 130 and the inner surface of the female coupling FC. Thereafter, for example, when the overlap therebetween is greater than or equal to the length X of the vent 130, for example about 4 millimeters, the outer surface 122 of the male coupling 120 and female coupling FC sealingly engage together. However, as depicted in FIGS. 14-16, the lumen extension tip LT still remains free from engagement with the inner surface of the male coupling 120 (e.g., the first section 126 and the transition section 127) to further reduce the volume of air within the recessed portion 124 prior to sealing engagement of an outer surface of the lumen extension tip LT with the transition section 127 and second interior section 128 (see FIG. 17). Further engagement of the tip cap 100 with the female coupling FC results in an end of the lumen extension tip LT being positioned substantially close to, and in example embodiments engaged with, the floor section 129 (see FIG. 18).

Thus, in comparison to the engagement of the tip cap 10 and the female coupling FC (see FIGS. 1-8), the tip cap 100 of the present invention comprises one or more vents 130 to postpone sealing engagement of the outer surface 122 of the male coupling 120 with the interior surface of the female coupling FC (e.g., thereby allowing more air to vent out). And, moreover, the interior surface of the reservoir 124 is preferably tapered in the transition section 127 to transition to the second interior section 128, which is preferably sized for providing sealing engagement with the outer surface of the lumen extension tip LT. Thus, in example embodiments, the vents 130 preferably terminate along a portion of the male coupling 120 and return to a sealing surface for providing sealing engagement with the interior surface of the female coupling FC. Furthermore, rather than allowing the compressed air to communicate with the open end of the conduit (23) of the lumen extension tip LT (shown in FIGS. 1-2), the second interior section 128 preferably provides for sealing engagement with the outer surface (OS) of the lumen extension tip LT, thereby preventing any of the compressed air within the annular void AV from exerting any pressure against the open end of the conduit of the lumen extension tip. Rather, only a small volume of air within the reservoir 124 is compressed (see FIGS. 17-18), which is insufficient to cause the plunger P to push back.

Figure 19:
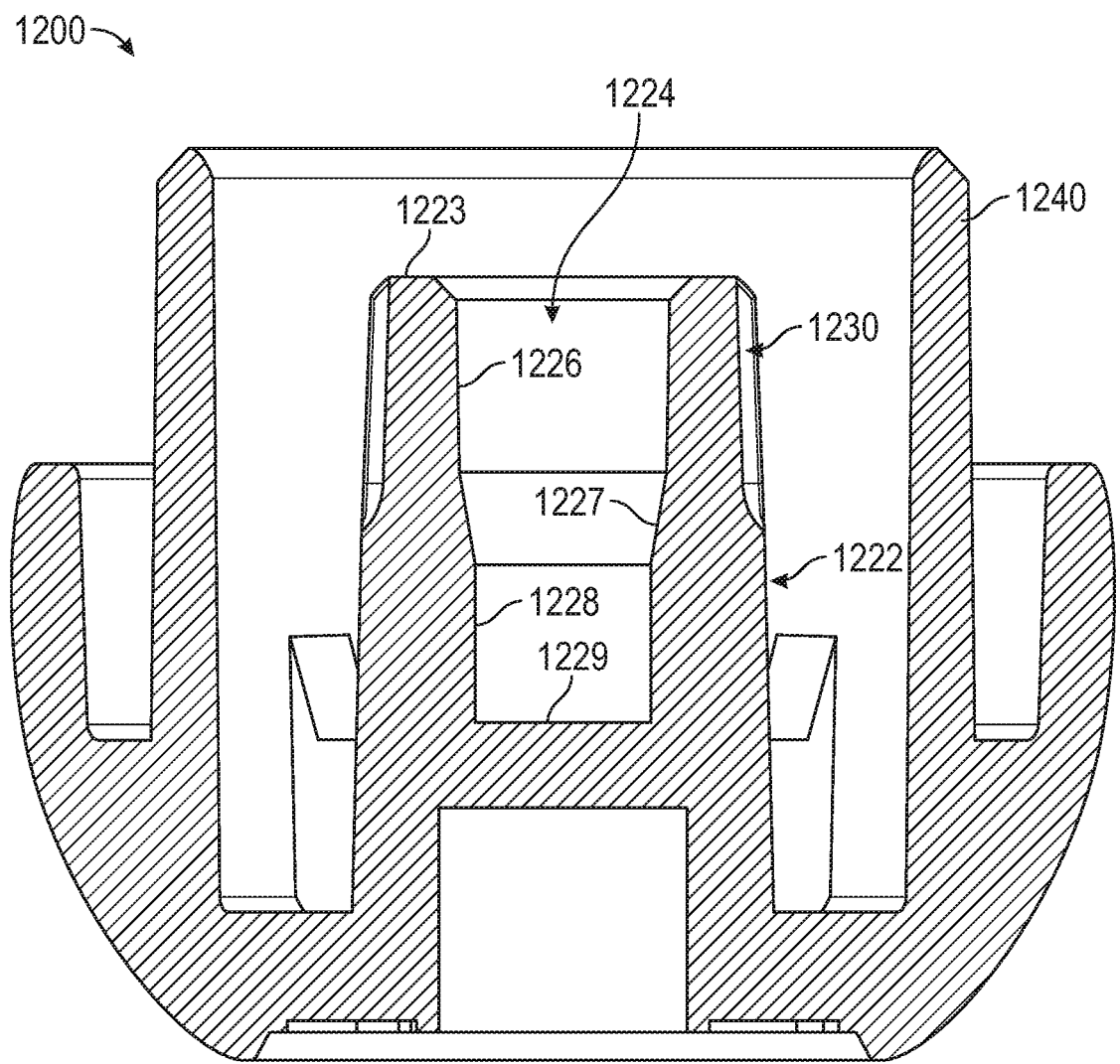
FIG. 19 is cross-sectional view of a schematic diagram of another tip cap according to another embodiment of the present disclosure.

According to one example embodiment, the tip cap 100 as described above can be modified for coupling engagement with only an interference fit, for example, a friction fit rather than providing one or more clips, threads or connectors for engagement with the lugs or threads of the syringe S. As depicted in FIG. 19, the tip cap 1200 can be configured such that an interference or friction fit causes sufficient engagement between the male coupling 1220 of the tip cap and the female coupling FC of the syringe S. In example embodiments, a collar 1240 is positioned to surround the male coupling 1220 and generally extend above an end surface 1223 of the male coupling 1220. In example embodiments, the collar 1240 comprises a substantially smooth interior surface (e.g., no ribs) and is generally sized to prevent interference with the threads or lugs that may be formed on an outer surface of the female coupling FC. As similarly described above, the male coupling 1220 comprises an outer surface 1222 that is configured for sealing engagement with an inner surface of the female coupling FC. Furthermore, as similarly described above, at least one recessed slot portion or grooved vent path 1230 is formed along the outer surface 1222 of the male coupling 1220, and the reservoir 1224 comprises an interior surface comprising a first interior section 1226, a transition section 1227, a second interior section 1228, and a floor section 1229.

According to some example embodiments, the one or more vents can be replaced with a texturized surface, for example, to allow for a plurality of micro channels to permit venting up to a point where the air that is trapped in the reservoir cannot be compressed to a point where plunger pushback occurs. According to some example embodiments, the entirety of the upper section of the male coupling is texturized. Optionally, the outer surface of the male coupling is texturized as desired. According to additional example embodiments of the present invention, venting (e.g., permitting air to escape from the annular void and reservoir) can be accomplished in a plurality of different ways. For example, as described herein, one or more vents may be formed on a portion of the male coupling, or for example, a textured surface can be provided on at least a portion of the male coupling to provide a plurality of micro ventilation channels. According to another example embodiment, one or more slots or channels can extend entirely through portions of the male coupling. According to another example embodiment, the male plug can have a non-circular geometry at the free end (e.g., near the end surface 1223) of the male coupling and fade or transition to have a circular geometry at an opposite end thereof for sealingly engaging with the interior surface of the outer collar of the female coupling FC. In example embodiments, the non-circular geometry can be generally square, triangular, oval, or another desired shape which would be incapable of sealing with the interior surface of the outer collar of the female coupling FC. According to another example embodiment, an end portion of the male coupling can comprise a chamfered or angled end which provides a transitional surface up to a point along the male coupling where the entirety thereof is substantially cylindrical and capable of sealingly engaging the interior surface of the outer collar of the female coupling. Optionally, other geometries can be provided as desired, for example, to provide a vent along a portion of the length, and then terminate and define a cylindrical sealing surface for engagement with the female coupling.

FIGS. 20-21 show another example embodiment of the present invention. In addition to providing one or more vents 130 on the male coupling 120 of the tip cap 100 (or other functional coupling that couples with the syringe S) as shown in FIGS. 8-20, the inner surface 1310 of the female coupling FC, for example on the syringe S, can optionally be provided with one or more vents 1330. The illustrated female coupling FC illustrates the general characteristics of an ISO-80369-3 compatible ENFit coupling, as understood in the industry. The vents 1330 have similar functions and geometries to the vents 130 described above. Similarly to the vents 130 in the tip cap 100 above, the vents 1330 in the female coupling FC extend from a distal connection end 1350 of the syringe S. Or, according to some example embodiments, the female coupling FC of the syringe S comprises one or more vents 1330 and the male coupling of the tip cap 100 does not comprise any vents. Or, according to another example embodiment, one of the components can comprise one or more vents and the other component can comprise a textured surface. Furthermore, a combination of both vents and a textured surface can be provided. In example embodiments, an outer surface 1320 of the lumen extension tip LT can be provided with one or more vents similar to the illustrated and described vents (not shown), a textured surface, and/or a combination of both. Thus, according to example embodiments, the venting features and mechanisms as described herein can alternatively be applied to the lumen extension tip (or outer collar of the female coupling FC) of the syringe or could optionally work in conjunction by being applied to both.

A plurality of alternative enteral components and connectors (see FIGS. 30-47 illustrated and described in U.S. Patent Application No. 62/620,576, hereinafter incorporated by reference) which can comprise one or more similar vent paths formed on the one or more male couplings can function similarly to the vented structures described above.

For example, a syringe-to-syringe coupler comprising oppositely opposing couplings which can comprise one or more vents as described above. In example embodiments, the male coupling comprises an ISO 80369-3 compatible coupling and the male coupling comprises a Legacy (i.e., non EnFit) coupling. Optionally, both coupling can be IS080369-3 compatible couplings comprising one or more vents. An additional syringe-to-syringe coupler comprising oppositely opposing male couplings can comprise one or more vents as described above. A plurality of oral administration couplers comprising male couplings can comprise one or more vents as described above. A vented enteral connector comprising a male coupling can comprise one or more vents as described above. A plurality of syringes comprising male couplings can comprise one or more vents as described above. Fluid transfer connectors comprising male couplings can comprise one or more vents as described above.

While the invention has been described with reference to example embodiments, it will be understood by those skilled in the art that a variety of modifications, additions and deletions are within the scope of the invention, as defined by the following claims.

What is claimed is:

1. An ISO 80369-3 compatible coupling configured for removable sealing engagement with an enteral syringe comprising a female coupling, an internal chamber and a plunger translating therein, the enteral syringe female coupling comprising a reservoir defined by an open distal end and a tapering inner surface, the ISO 80369-3 compatible coupling comprising:

a male coupler comprising a tapering outer surface and a reservoir defined by an open distal end and an inner surface, the inner surface comprising a first section, a transition section, and a second section, wherein the first section is wider than the second section and the transition section is disposed between the first section and the second section, wherein the male coupler is oriented along a connection axis, wherein the male coupler tapering outer surface is configured for removable sealing engagement with an enteral syringe female coupling tapering inner surface along a connection axis, further wherein the male coupler reservoir is configured to receive a volume of air;

wherein the male coupler tapering outer surface comprises at least one vent configured to release an amount of the volume of air present in the male coupling reservoir during engagement between the ISO 80369-3 compatible coupling and the enteral syringe, wherein the at least one vent comprises a maximum depth from the tapering outer surface at a top end of the at least one vent and a minimum depth at a closed end of the at least one vent, further wherein the at least one vent comprises a tapered transition from the maximum depth to the closed end.

2. The ISO 80369-3 compatible coupling of claim 1, wherein the male coupler tapering outer surface extends between a base end and a free end, wherein the at least one vent extends along the male coupler tapering outer surface from the free end toward the base end.

3. The ISO 80369-3 compatible coupling of claim 1, wherein the male coupler tapering outer surface defines a range of diameters between a maximum diameter at a base end and a minimum diameter at a free end, the at least one vent being recessed from the range of diameters of the male coupler tapering outer surface.

4. The ISO 80369-3 compatible coupling of claim 3, wherein the male coupler tapering outer surface range of diameters corresponds opposingly with the enteral syringe female coupling tapering inner surface, the at least one vent configured to be removed from sealing engagement with the enteral syringe female coupling tapering inner surface.

5. The ISO 80369-3 compatible coupling of claim 1, wherein the at least one vent extends a distance along the tapering outer surface from a position relative to the connection axis in alignment with the open distal tip to a position relative to the connection axis in alignment with the inner surface transition section.

6. The ISO 80369-3 compatible coupling of claim 1, wherein the at least one vent comprises two or more vents.

7. The ISO 80369-3 compatible coupling of claim 1, wherein the at least one vent comprises a surface configured to be removed from engagement with the enteral syringe female coupling tapering inner surface during engagement between the ISO 80369-3 compatible coupling and the enteral syringe.

8. The ISO 80369-3 compatible coupling of claim 1, wherein the at least one vent comprises a groove recessed from the male coupler tapering outer surface.

9. The ISO 80369-3 compatible coupling of claim 1, wherein the at least one vent comprises a texturized surface different from the male coupler tapering outer surface.

10. The ISO 80369-3 compatible coupling of claim 1, wherein the at least one vent extends along a linear path relative to the connection axis.

11. The ISO 80369-3 compatible coupling of claim 1, wherein the at least one vent extends along a non-linear path relative to the connection axis.

12. The ISO 80369-3 compatible coupling of claim 11, wherein the at least one vent extends along a helical path around the male coupler tapering outer surface.

13. The ISO 80369-3 compatible coupling of claim 1, wherein the at least one vent comprises a length relative to the connection axis of between about 1.5 mm and 6.0 mm.

14. The ISO 80369-3 compatible coupling of claim 1, wherein the at least one vent comprises a width relative to the connection axis of between about 0.125 mm and 5.0 mm.

15. The ISO 80369-3 compatible coupling of claim 1, wherein the at least one vent comprises a depth from the male coupler tapering outer surface of between about 0.1 mm and 1.0 mm.

16. The ISO 80369-3 compatible coupling of claim 1, further comprising a collar oriented about the connection axis, wherein the collar is configured to fasten to the enteral syringe female coupling.

17. The ISO 80369-3 compatible coupling of claim 16, wherein the collar comprises threading.

18. The ISO 80369-3 compatible coupling of claim 16, wherein the collar comprises a smooth inner surface that is configured to fasten to the enteral syringe female coupling with an interference fit.

19. The ISO 80369-3 compatible coupling of claim 1, wherein the ISO 80369-3 formatted coupling is part of a syringe cap.

20. The ISO 80369-3 compatible coupling of claim 1, wherein the ISO 80369-3 formatted coupling is part of a syringe-to-syringe coupler.

21. The ISO 80369-3 compatible coupling of claim 1, wherein the ISO 80369-3 formatted coupling is part of oral administration coupler.

22. A male coupling oriented along a connection axis and configured for removable sealing engagement with a female coupling comprising a reservoir defined by a tapering inner surface extending between a narrowest closed end and a widest open end, the female coupler reservoir is configured to receive a volume of air, the male coupling comprising:
   a tapering outer surface extending between a widest fixed end and a narrowest distal tip, and a reservoir defined by an inner surface extending between a closed floor and an open distal end, the inner surface comprising a first section, a transition section, and a second section, wherein the first section is wider than the second section and the transition section is disposed between the first section and the second section, wherein the coupler tapering outer surface is configured for removable sealing engagement with a female coupling tapering inner surface along the connection axis, further wherein the male coupler reservoir is configured to receive a volume of air;
   wherein the male coupling tapering outer surface comprises at least one vent configured to permit an amount of the volume of air present in the male coupling reservoir and an amount of a volume of air present in the reservoir of the female coupling to escape during engagement between the male coupling and the female coupling, the at least one vent extending from the tapering outer surface distal tip towards the proximal end, wherein the at least one vent is configured to provide a flow pathway between the male coupling tapering outer surface and the female coupling tapering inner surface to permit the volumes of air in the male and female couplings to escape therethrough,
   wherein the at least one vent comprises a maximum depth from the tapering outer surface at a top opening of the at least one vent and a minimum depth at a closed end of the at least one vent, further wherein the at least one vent comprises a tapered transition from the maximum depth to the closed end.

23. The male coupling of claim 22, wherein the at least one vent of the male coupler tapering outer surface comprises a plurality of the vents.

24. The male coupling of claim 22, wherein the at least one vent comprises a surface configured to be removed from engagement with the female coupling tapering inner surface during engagement between the male coupling and the female coupling.

25. The male coupling of claim 22, wherein the at least one vent comprises a groove recessed from the male coupler tapering outer surface.

26. The male coupling of claim 22, wherein the at least one vent comprises a texturized surface different from the male coupling tapering outer surface.

27. The male coupling of claim 22, wherein the at least one vent extends along a linear path relative to the connection axis.

28. The male coupling of claim 22, wherein the at least one vent extends along a non-linear path relative to the connection axis.

* * * * *